Figure 1A:
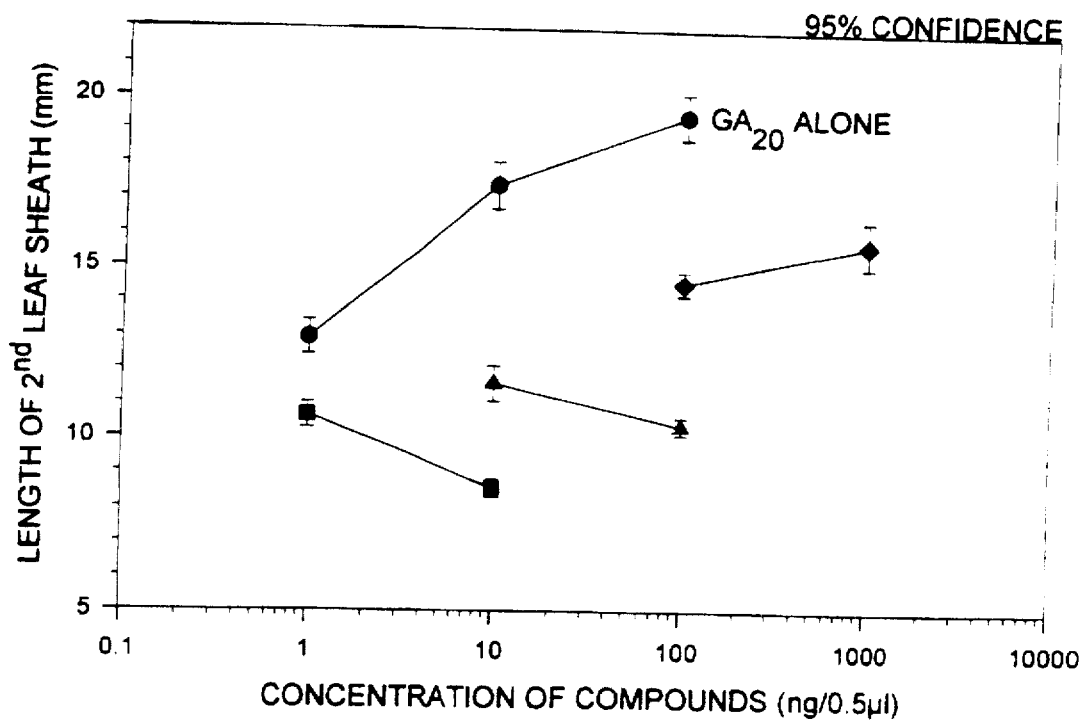

United States Patent [19]

Pharis et al.

[11] Patent Number: 5,767,042
[45] Date of Patent: Jun. 16, 1998

[54] RING D-MODIFIED GIBBERELLIN COMPOUNDS, AND PREPARATION AND USE THEREOF

[75] Inventors: Richard Persons Pharis, Cochrane, Canada; Lewis Norman Mander, Aranda; Roderick Whitfield King, Deakin, both of Australia

[73] Assignees: The Australian National University; Commonwealth Scientific and Industrial Research Organization, both of Australia; Richard P. Pharis, Alberta, Canada

[21] Appl. No.: 793,519

[22] PCT Filed: Aug. 25, 1995

[86] PCT No.: PCT/AU95/00528

§ 371 Date: May 8, 1997

§ 102(e) Date: May 8, 1997

[87] PCT Pub. No.: WO96/06090

PCT Pub. Date: Feb. 29, 1996

[30] Foreign Application Priority Data

Aug. 25, 1994 [AU] Australia .................. PM7666

[51] Int. Cl.⁶ ............................................. C07D 307/77
[52] U.S. Cl. ...................... 504/297; 549/298; 549/299
[58] Field of Search .......................... 549/298, 299; 504/297

[56] References Cited

FOREIGN PATENT DOCUMENTS 24440   3/1993   Australia .

OTHER PUBLICATIONS

March, J. *Adv. Org Chem* (1977) p. 794.

*Primary Examiner*—Amelia Owens
*Attorney, Agent, or Firm*—Birch, Stewart, Kolasch & Birch, LLP

[57] ABSTRACT

Ring D-modified gibberellin compounds are effective in promoting or inducing a desired tissue morphology and/or physiological state in plants, giving effects such as growth retardation or inhibition and inhibition of floral development.

10 Claims, 1 Drawing Sheet

RING D-MODIFIED GIBBERELLIN COMPOUNDS, AND PREPARATION AND USE THEREOF

This application is a 371 of PCT/AU95/00528 filed Aug. 25, 1995.

This invention relates to ring D-modified gibberellin compounds, to processes for the production thereof, and to methods of use of these compounds.

As disclosed in prior International Patent Application No. PCT/AU92/00426 (WO 93/03616), numerous phytoactive substances are known, including the C-16,17-dihydro gibberellins, which can be used in agricultural and horticultural practice in order to promote desired physiological effects in higher plants. Such effects include promotion of flowering, inhibition of flowering, inhibition of seed head formation, weed control, inhibition of stem elongation (dwarfing), improvement of hardiness, promotion of rooting and inhibition of root or shoot growth in germinating seeds. Unfortunately, most available phytoactive substances have undesirable side effects and may give rise to toxic residues which tend to pollute the environment.

Gibberellins (GAs) are known to influence both growth and flowering in many plants, particularly in those requiring exposure to long days for flowering (Lang, 1965; Zeevaart, 1983; Pharis & King, 1985). The grass *Lolium temulentum* is such a long day (LD) plant (Evans, 1964, 1969), and recent studies with that species have revealed quite different structural requirements for the promotion of stem elongation on the one hand and floral inflorescence initiation on the other (Evans et al., 1990). The different structural requirements of these two processes were even more apparent in experiments with C-16,17 dihydro derivatives of several GAs, especially of $GA_5$ and $GA_{20}$, where at optimal doses they promoted flowering, but inhibited stem elongation by up to 40% (Evans et al., 1994b). Such a combination of effects also is of horticultural significance. Additionally, it has also been reported that the C-16,17-dihydro gibberellins can reduce leaf and leaf sheath elongation in rice (Takagi et al., 1994).

At doses which gave good inhibition of stem elongation, flowering of Lolium was not inhibited by C-16,17-dihydro gibberellins (Evans et al., 1994b) and could be promoted both by these gibberellins and by the gibberellin biosynthesis inhibitor CGA 163935. As found with CGA 163935 (Adams et al., 1992), these C-16,17-dihydro gibberellins apparently act to block late steps in gibberellin biosynthesis (Takagi et al., 1994).

Suppression of turfgrass by various growth retarding chemicals has been widely reported both for warm- and cool-season grass mixtures (Kaufman, 1990). However, responses have not always been consistent, yellowing may result (Sander and Hensley, 1993) and the growth retardant used may not be environmentally acceptable. The type of growth suppression varies with the chemical used, maleic hydrazide and mefluidide causing shoot mortality with rapid proliferation of new shoots whilst flurprimidol and paclobutrazol only suppress foliar growth (Spak et al., 1993). Seedhead suppression is also desirable and Johnson (1990, 1993) reported beneficial responses with imazethapyn, mefluidide and prinexapacethyl (Primo™ or CGA 163935) on centipede grass. In the case of CGA 163935, high doses were required and this led to foliar damage.

The objective in many turf management situations is to maintain a dense turf with active photosynthesis, leaf formation and tillering but with reduced leaf elongation and prevention of inflorescence formation. Repeated mowing is an expensive—and sometime hazardous—solution, and a compound which reduces stem and leaf elongation without reducing photosynthesis, leaf appearance rate, leaf longevity and plant viability is highly desirable.

Prior International Application No. PCT/AU92/00426 discloses a method of treatment comprising the application to a plant or to plant tissues (including cuttings, roots, bulbs, corms, tubers, rhizomes and seeds) of a C-16,17-dihydro gibberellin or a C-16,17-dihydro gibberellin precursor effective to produce an at least partial inhibition of the formation of effector gibberellins that cause growth and development in the plant in order to induce a desired tissue morphology and/or a desired physiological state. Effects obtained in accordance with the use of those compounds include dwarfing, stem and shoot and/or root (radicle) growth retardation, flowering, improved fruit quality, inhibited fruit ripening, improved fruit set, controlled weed growth, induced male sterility, retarded bud break and tillering.

The present invention relates to novel ring D-modified gibberellin compounds which have also been found to have use in inducing a desired tissue morphology and/or a desired physiological state in plants giving effects as described above.

According to one aspect of the present invention, there are provided ring D-modified gibberellin compounds of the general formulae IA or IB, as follows:

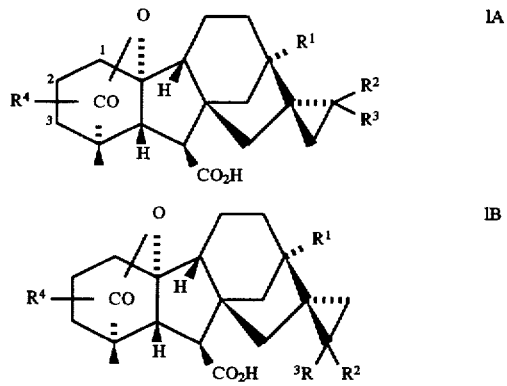

wherein $R^1$ represents H or OH; and $R^2$ and $R^3$, which may be the same or different, each represents H, F, Cl, Br, lower ($C_{1-6}$) alkyl, lower ($C_{2-6}$) alkenyl or lower ($C_{3-6}$) cycloalkyl;

and wherein $R^4$ indicates that the A ring may be (i) unfunctionalised, or (ii) contain a 1,2-double bond or 2,3-double bond, or (iii) contain a 3α- or 3β-OH, F, Cl or Br group with or without a 1,2-double bond, or (iv) contain a 1α- or 1β-OH, F, Cl or Br group with or without a 2,3-double bond.

In another aspect, the present invention also provides ring D-modified gibberellin compounds of the general formula IC as follows:

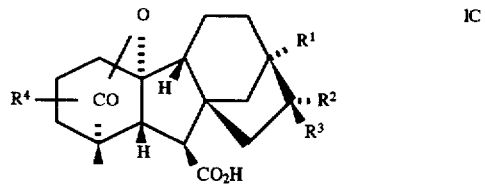

wherein $R^1$ represents H or OH; and $R^2$ and $R^3$, which may be the same or different, each represents H, F, Cl, Br, lower ($C_{1-6}$) alkyl, lower ($C_{2-6}$) alkenyl, lower ($C_{3-6}$) cycloalkyl, or $CH_2X$ (wherein X is F, Cl or Br);

and wherein $R^4$ indicates that the A ring may be (i) unfunctionalised, or (ii) contain a 1,2-double bond or 2,3-double bond, or (iii) contain a 3α- or 3β-OH, F, Cl or Br group with or without a 1,2-double bond, or (iv) contain a 1α- or 1β-OH, F, Cl or Br group with or without a 2,3-double bond;
with the proviso that:

(i) $R^2$ and $R^3$ are not both H;

(ii) if $R^2$ is H then $R^3$ is not methyl, and if $R^3$ is H then $R^2$ is not methyl;

(iii) $R^2$ is not Cl or Br when $R^3$ is chloromethyl or bromomethyl and the A ring contains a 3β-OH, and $R^3$ is not Cl or Br when $R^2$ is chloromethyl or bromomethyl and the A ring contains a 3β-OH.

The present invention also extends to simple esters (e.g. lower carboxylic acid esters) and ethers (e.g. lower alkyl or substituted lower alkyl ethers) of compounds of general formulae IA to IC having 1-OH, 3-OH and/or 13-OH groups, and/or to simple esters (e.g. lower alkyl and substituted lower alkyl esters) and salts (e.g. alkali and alkaline earth metal salts) of compounds of general formulae IA to IC having 7-COOH groups.

Whilst the compounds of the present invention fall within a number of the gibberellin series, including the $GA_1$, $GA_4$, $GA_7$ and $GA_9$ series, particularly preferred compounds of the present invention are compounds of the $GA_5$, $GA_{20}$ and $GA_3$ gibberellin series, including the following:

The compounds of the present invention, and in particular the compounds of the invention which are of the $GA_3$, $GA_5$ and $GA20$ gibberellin series, may in general be prepared by a two step method from a parent alkene, such as gibberellic acid ($GA_3$), involving a dihalocarbene addition followed by reductive dehalogenation, as follows:

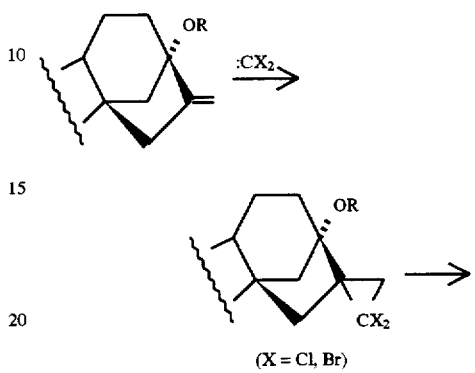

(X = Cl, Br)

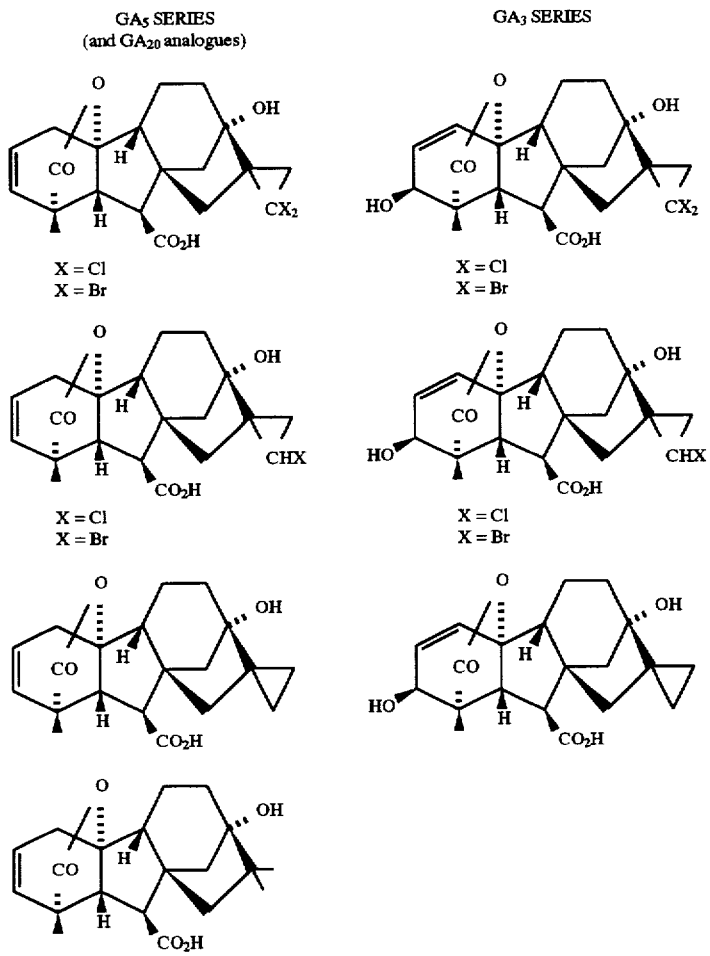

-continued

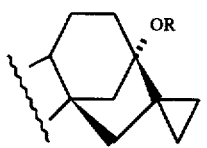

Partial reduction of dihalocyclopropanes to monohalocyclopropanes is a well known reaction (for example, using tributyltin hydride), whilst complete reduction of the dihalocyclopropanes readily yields the cyclopropyl derivatives (particularly using the dibromocyclopropanes). The cyclopropyl derivatives may be cleaved by hydrogenolysis.

An effective overall scheme involves the preparation of a common intermediate from $GA_3$ which can then be taken on to make both $GA_3$ and $GA_5$ (and $GA_{20}$) type compounds. Simple deprotection then affords the $GA_3$ derivatives. The steps in the known conversion of $GA_3$ into $GA_5$ (and $GA_{20}$) are then incorporated into the synthesis of the required $GA_5$ (and $GA_{20}$) derivatives:

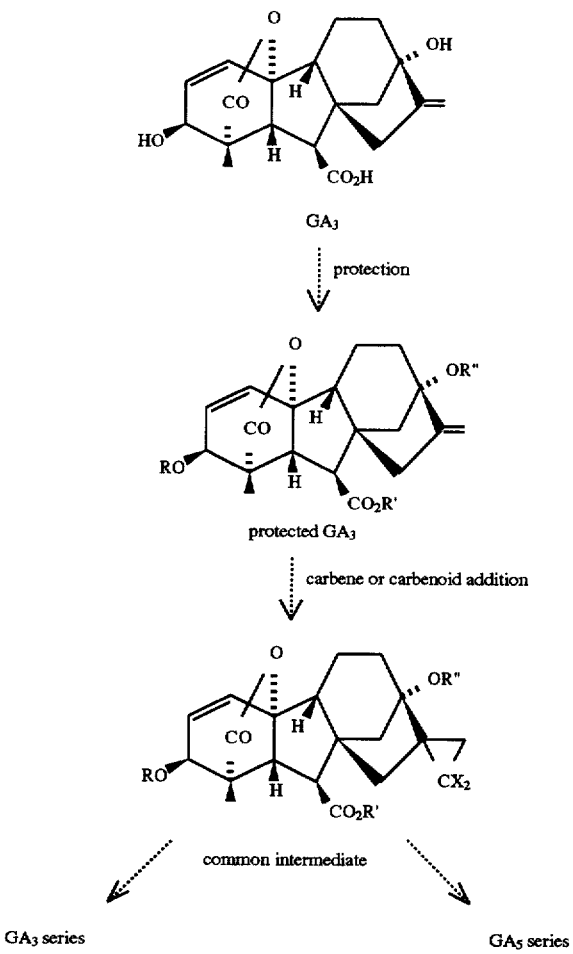

The Examples below illustrate typical reaction schemes for the preparation of compounds of the $GA_3$ and $GA_5$ gibberellin series having the general formulae IA to IC. Other compounds of these general formulae may be prepared by analogous reaction schemes and/or by reactions which are well known per se to persons skilled in this field.

As noted above, the compounds of the present invention have been found to have use in inducing a desired tissue morphology and/or a desired physiological state in plants.

By way of example only, compounds of the present invention have been shown to inhibit shoot growth of temperate turf grasses including Kentucky Blue Grass, fine leaf rye and tall fescue. They may also be effective in selective removal of annual grassy weeds (such as *Poa annua*) in swards of perennial turf grasses, while keeping the sward green during the first season when seed head formation is prevented and/or sterility induced. Compounds of the present invention have also been shown to have effects on floral development and/or stem elongation in the grass *Lolium temulentum* and to inhibit sheath and leaf elongation of rice. More generally, the effects of these compounds may be seen as herbicides and sterilants. They may also show specificity between monocotyledonous and dicotyledonous plants.

Accordingly, in another aspect the present invention provides a method for promoting or inducing a desired tissue morphology and/or physiological state in a plant, which comprises applying to the plant or plant tissue (including cuttings, roots, bulbs, corms, tubers, rhizomes or seeds) an effective amount of a compound of the general formulae IA to IC as defined above.

In this aspect, the present invention also extends to a composition for the treatment of plants or plant tissue, which comprises an effective amount of a compound of the general formula IA to IC as defined above, together with an agriculturally- or horticulturally-acceptable carrier or diluent.

The term "effective amount" as used herein means an amount which is effective in promoting or inducing a desired tissue morphology and/or physiological state in the plants or plant tissue being treated.

Further, in this aspect the invention also extends to the use of a compound of the general formulae IA to IC as defined above in promoting or inducing a desired tissue morphology and/or physiological state in a plant.

The method of application of the compounds of the present invention to the plant or plant tissue is not thought to be particularly critical and may be accomplished, for example, by spraying a solution or suspension of the compound to whole plants, or by application to seeds or roots or bulbs, corms or rhizomes, together with a suitable carrier. The addition of conventional adjuvants such as wetting agents and dispersants may prove to be beneficial in some agronomic situations.

Only small quantities of the active compound need be applied in accordance with the invention. The precise dose or effective amount will depend upon the desired tissue morphology or physiological state which is desired to be induced and the plant species. For a given species, the required dosage and treatment regime can readily be determined by carrying out appropriate experiments, e.g. along the lines of those described herein.

As a general guide, dosage rates of from 0.01 to 1000 micrograms of compound per gram of actively growing plant tissue, especially from 2 to 100 micrograms of compound per gram of actively growing plant tissue may give useful results, although satisfactory results may be obtained with as little as 0.01 micrograms per plant. Effective amounts of active compound may be from 1 to 1000 grams per hectare.

The amount of active compound applied in accordance with the invention may also be expressed in terms of a proportion of the weight of fresh or dry plant tissue. Expressed in this way, the applied amount may be up to 1000 micrograms/gram fresh weight, especially from 1 to 1000 micrograms/gram fresh weight. Most preferably, the amounts applied are from 2 to 1000 micrograms/gram fresh weight, especially from 2 to 500 micrograms/gram fresh weight. Optimally, the applied amounts are from 2 to 333 micrograms/gram fresh weight, especially from 2 to 100 micrograms/gram fresh weight. (For most plant species, the ratio of fresh:dry weights is 10:1–6:1).

The compounds may be formulated for use in accordance with this invention at concentrations up to 5000 ppm (1.5× $10^{12}$M). Most preferably the minimum concentration is preferably 0.1 ppm (when applied as a seed soak or soil drench, lower concentrations may be used as detailed below). A preferred concentration range is 1–1000 ppm.

Concentrations of from 1–500 ppm, preferably from 1–350 ppm, may give satisfactory results, especially when applied as a foliar spray. With certain species, application rates of from 10 to 100 times higher than those mentioned above may be required. Lower concentrations have been found to be effective when used as a seed soak or soil drench, for example concentrations in the range of $10^{-14}$ to $10^{-7}$ molar, although preferably the minimum concentration is at least $10^{-10}$M.

Although the method of the invention can be carried out using a compound of the general formulae IA to IC as defined above as the sole plant growth modifying agent, other plant growth regulators such as cytokinins or even shoot elongation-promotive gibberellins such as gibberellin $A_1$, $A_3$, $A_4$, $A_7$, and/or $A_9$ may be additionally used.

Throughout this specification, unless the context requires otherwise, the word "comprise", or variations such as "comprises" or "comprising", will be understood to imply the inclusion of a stated integer or group of integers but not the exclusion of any other integer or group of integers.

The compounds of the present invention and processes for the preparation thereof, and methods of use thereof are illustrated by way of example in the following, non-limiting Examples.

EXAMPLE 1

Gibberellic Acid 3-Acetate (2)

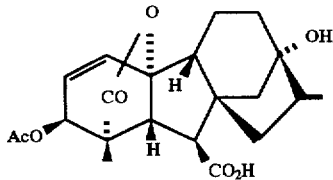

Gibberellic acid is available from commercial sources. The 3-acetate 2 is prepared as described by B. E. Cross (J Chem Soc., 1954, 4670).

EXAMPLE 2 ent-3α-Acetoxy-13-hydroxy-20-norgibberell-1,16-diene-7,19-dioic Acid 19,10-Lactone 7-Methoxymethyl Ester (3)

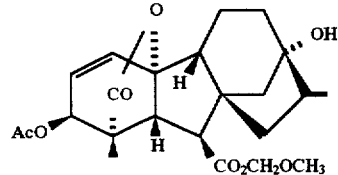

A solution of gibberellic acid 3-acetate 2 (23 g, 0.06 mol) in dichloromethane (250 ml) was treated with diisopropyl-ethylamine (14 ml, 0.08 mol) and methoxymethyl chloride (4.5 ml, 0.06 mol), and the mixture kept under a nitrogen atmosphere at 4° C. for 14 h. Saturated sodium bicarbonate was added and the product extracted into dichloromethane. The organic layer was washed with 2N HCl, water, sodium bicarbonate solution, brine and dried over sodium sulfate. After removal of solvent, the residue was chromatographed on silica gel and acetate 3 (22 g), 86% yield) eluted with ethyl acetate/hexane (1:1). $^1$H NMR (CDCl$_3$): 1.16 (3H, s, H18); 2.10 (3H, s, OCOCH$_3$); 2.79 (1H, d, $J_{6,5}$=10.9 Hz, H6);3.33 (1H, d, $J_{5,6}$=10.9 Hz, H5); 3.47 (3H, s, CO$_2$CH$_2$OCH$_3$); 4.96 (1H, s, H17); 5.26 (1H, d, J=5.4 Hz CO$_2$CH$_2$OCH$_3$); 5.27 (1H, S, H17); 5.29 (1H, d, J=6.1 Hz, CO$_2$CH$_2$OCH$_3$); 5.33 (1H, d, $J_{3,2}$=3.8 Hz, H3); 6.38 (1H, d, $J_{1,2}$=9.3 Hz, H1)

EXAMPLE 3 ent-3α-Acetoxy-16β,17-dichloromethano-13-hydroxy-20-norgibberell-1-ene-7,19-dioic Acid 19, 10-Lactone 7-Methoxymethyl Ester (4)

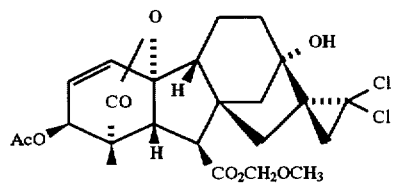

To a solution of ester 3 (5.3 g, 0.012 mol) in chloroform (100 ml) under an atmosphere of nitrogen was quickly added powdered sodium hydroxide (4.0 g, 0.1 mol) followed by benzyltriethylammonium chloride (100 mg) and stirring continued for 40 min. The temperature of the mixture was kept below 30° C. by occasional cooling with an external ice-water bath. Further powdered sodium hydroxide (2 6, 0.05 mol) was added and stirring continued for a further 40 min. The mixture was filtered through celite, washed with sodium dihydrogenphosphate solution (20%), dried over sodium sulfate, concentrated and chromatographed on silica, eluting with ethyl acetate/petroleum ether (40°–60° C.) (1:1) to afford the adduct 4 (4 g, 63% yield) as a white foam. $^1$H NMR (CDCl$_3$): 1.17 (3H, s, H18); 1.39 (1H, d, $J_{17,17}$=7.5 Hz, H17); 1.74 (1H, d, $J_{17,17}$=7.5 Hz, HO17); 2.09 (3H, s, OCOCH$_3$); 2.81 (1H, d, $J_{6,5}$=10.5 Hz, H6); 3.31 (1H, d, $J_{5,6}$=10.5 Hz, H5); 3.52 (3H, s, CO$_2$CH$_2$OCH$_3$); 5.28 (1H, d, J=6.1 Hz, CO$_2$CH$_2$OCH$_3$); 5.33 (1H, d, J=6.1 Hz, CO$_2$CH$_2$OCH$_3$); 5.34 (1H, s, H3); 5.88 (1H, dd, $J_{2,1}$=9.3 Hz, $J_{2,3}$=3.8 Hz, H2); 6.39 (1H, d, $J_1$=9.3 Hz, H1)

EXAMPLE 4 ent-3α,13-Diacetoxy-16β,17-dichloromethano-20-norgibberell-1-ene-7,19-dioic Acid 19,10-Lactone 7-Methoxymethyl Ester (5)

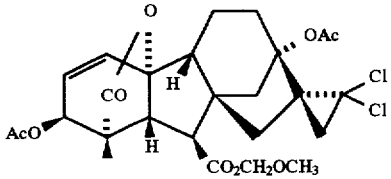

A solution of the ester 4 (8.6 g, 16.7 mmol) in dichloromethane (45 ml) and triethylamine (5.07 g) was cooled in an ice bath and then treated dropwise with acetic anhydride (5.1 g), followed by 4-N,N'-dimethylaminopyridine (150 mg). This solution was stored at 5° C. for 48 h. After cooling in an ice bath a small amount of ice was added to the reaction mixture and stirring continued for 5 min. The addition was repeated once and then several grams of ice were added. Stirring was continued at room temperature for 15 min., most of the dichloromethane removed on a rotary evaporator, then ethyl acetate was added. The organic layer was washed with cold 2N HCl, water, sodium bicarbonate solution, brine and dried over sodium sulfate. Removal of solvent afforded diacetate 5 as a crystalline solid (9.2 g, 100%). $^1$H NMR (CDCl$_3$): 1.16 (3H, s, H18); 1.39 (1H, d, $J_{17,17}$=7.4 Hz, H17); 1.81 (1H, d, $J_{17,17}$=7.4 Hz, HO17); 1.98 (3H, s, OCOCH$_3$); 2.09 (3H, s, OCOCH$_3$); 2.81 (1H, d, $J_{6,5}$=10.8 Hz, H6); 3.32 (1H, d, $J_{5,6}$=10.8 Hz, H5); 3.56 (3H, s, CO$_2$CH$_2$OCH$_3$); 5.23 (1H, d, J=6.0 Hz, CO$_2$CH$_2$OCH$_3$); 5.32 (1H, d, $J_{3,2}$=3.85 Hz, H3); 5.38 (1H, d, J=6.0 Hz, CO$_2$CH$_2$OCH$_3$); 5.88 (1H, dd, $J_{2,1}$=9.4 Hz, $J_{2,3}$=3.8 Hz, H2); 6.38 (1H, d, J=9.4 Hz, H1)

EXAMPLE 5 ent-13-Acetoxy-16β,17-dichloromethano-3α-hydroxy-20-norgibberellane-7,19-dioic Acid 19,10-Lactone 7-Methoxymethyl Ester (6)

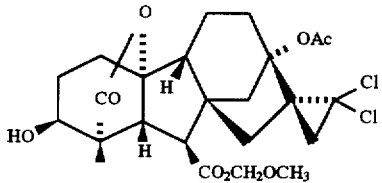

A solution of diacetate 5 (2 g, 3.34 mmol) in methanol (130 ml) was treated with a solution of potassium carbonate (0.75 g) and potassium hydrogen carbonate (0.63 g) in water (25 ml) and the resulting cloudy mixture stirred for 30 min. at room temperature, by which time a clear solution had been obtained. The pH was brought to 7 by the addition of acetic acid and the excess of solvent removed on a rotary evaporator. The residue was extracted with ethyl acetate and the resulting solution washed with aqueous potassium carbonate, brine and dried over sodium sulfate. Removal of solvent afforded ent-13-acetoxy-16β,17-dichloromethano-3β-hydroxy-20-norgibberell-1-ene-7,19-dioic acid 19,10-lactone 7-methoxymethyl ester as a white crystalline solid (1.8 g). $^1$H NMR: 1.27 (3H, s, H18); 1.41 (1H, d, $J_{17,17}$=7.3 Hz, H17); 1.81 (1H, d, $J_{17,17}$=7.3 Hz, HO17); 2.00 (3H, s, OCOCH$_3$); 2.83 (1H, d, $J_{6,5}$=10.8 Hz, H6); 3.21 (1H, d, $J_{5,6}$=10.8 Hz, H5); 3.60 (3H, s, CO$_2$CH$_2$OCH$_3$); 4.16 (1H, d, $J_{3,2}$=3.7 Hz, H3); 5.23 (1H, d, J=6.0 Hz, CO$_2$CH$_2$OCH$_3$); 5.38 (1H, d, J=6.0 Hz, CO$_2$CH$_2$OCH$_3$); 5.92 (1H, dd, $J_{2,1}$=9.3 Hz, $J_{2,3}$=3.7 Hz, H2); 6.32 (1H, d, $J_{1,2}$=9.3 Hz, H1). This material was dissolved in ethyl acetate (50 ml), 5% rhodium-alumina (0.25 g) added, and the mixture stirred under a hydrogen atmosphere for 16 h. The filtered mixture was reduced to dryness and chromatographed on silica gel, eluting with ethyl acetate/petroleum ether (40°–60°) (1:1) to afford the 3β-carbinol 6 (65% yield). $^1$H NMR (CDCl$_3$): 1.13 (3H, s, H18); 1.39 (1H, d, $J_{17,17}$=7.3 Hz, H17); 1.76 (1H, d, $J_{17,17}$=7.3 Hz, HO17); 1.96 (3H, s, OCOCH$_3$); 2.70 (1H, d, $J_{6,5}$=10.3 Hz, H6); 3.19 (1H, d, $J_{5,6}$=10.3 Hz, H5); 3.52 (3H, s, CO$_2$CH$_2$OCH$_3$); 3.81 (1H, br s, H3); 5.18 (1H, d, J=6.0 Hz, CO$_2$CH$_2$OCH$_3$); 5.32 (1H, d, J=6.0 Hz, CO$_2$CH$_2$OCH$_3$)

EXAMPLE 6 ent-13-Acetoxy-16β,17-dichloromethano-3α-mesyloxy-20-norgibberellane-7,19-dioic Acid 19, 10-Lactone 7-Methoxymethyl Ester (7)

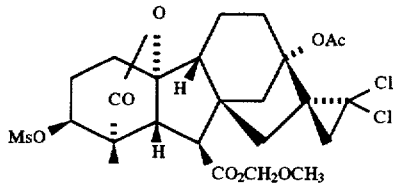

To a stirred solution of carbinol 6 (5.2 g, 10 mmol) in dry dichloromethane (30 ml) at 4° C. under a nitrogen atmosphere was added triethylamine (2.79 ml, 20 mmol) followed by dropwise addition of methanesulfonyl chloride (1.54 ml, 20 mmol). After 30 min. a piece of ice was added and the mixture stirred for 15 min. Further ice was then added, stirring continued for 10 min., and the temperature allowed to rise to ambient. The mixture was diluted with ethyl acetate, washed with potassium dihydrogenphosphate (20%), brine, potassium carbonate solution (10%), and dried over sodium sulfate. Removal of solvent and chromatography on silica gel, eluting with ethyl acetate/petroleum ether (40°–60°) (1:1.5), afforded mesylate 7 (5.1 g, 85% yield). $^1$H NMR (CDCl$_3$): 1.19 (3H, s, H18); 1.39 (1H, d, $J_{17,17}$=7.3 Hz, H17); 1.77 (1H, d, $J_{17,17}$=7.3 Hz, HO17); 1.96 (3H, s, OCOCH$_3$); 2.71 (1H, d, $J_{6,5}$=10.3 Hz, H6); 3.07 (3H, s, OSO$_2$CH$_3$); 3.13 (1H, d, $J_{5,6}$=10.3 Hz); 3.54 (3H, S, CO$_2$CH$_2$OCH$_3$); 4.74 (1H, br d, J=2.2 Hz, H3); 5.21 (1H, d, J=5.5 Hz, CO$_2$CH$_2$OCH$_3$); 5.35 (1H, d, J=5.5 Hz, CO$_2$CH$_2$OCH$_3$).

EXAMPLE 7 ent-13-Acetoxy-16β,17-dichloromethano-20-norgibberell-2-ene-7,19-dioic Acid 19,10-Lactone (8)

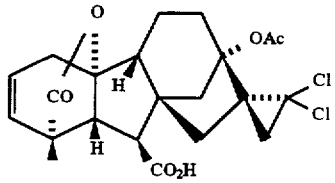

Mesylate 7 (5.1 g, 8.56 mmol) was dissolved in toluene (100 ml, distilled from calcium hydride), DBU (6.52 g, 42.8 mmol) added, and the solution heated at 120° C. under an atmosphere of nitrogen for 34 h. The cooled solution was extracted with potassium carbonate solution and the extracts acidified with 1N HCl, and the product extracted into ethyl acetate. The organic layer was washed with water until neutral, dried (sodium sulfate) and reduced to dryness, affording acid 8 (2.77 g, 71%). $^1$H NMR (CDCl$_3$): 1.27 (3H, s, H18); 1.38 (1H, d, $J_{17,17}$=7.3 Hz, H17); 1.78 (1H, d, $J_{17,17}$=7.3 Hz, H17); 1.97 (3H, s, OCOCH$_3$); 2.68 (1H, d, $J_{6,5}$=9.4 Hz, H5); 2.73 (1H, d, $J_{5,6}$=9.4 Hz, H6); 5.67 (1H, br d, J=9.3 Hz, H3); 5.80 (1H, d tr, J=9.3 Hz, J=2.9 Hz, H2)=9.3 Hz, J=2.9 Hz, H2)

EXAMPLE 8 ent-16β,17-Dichloromethano-13-hydroxy-20-norgibberell-2-ene-7,19-dioic Acid 19,10-Lactone (9)

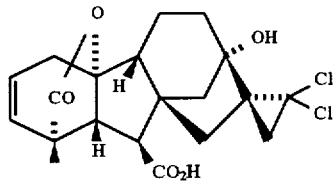

Acetate 8 (2.25 g, 4.94 mmol) was dissolved in methanol (100 ml), potassium carbonate (3.4 g, 24.7 mmol) added and the mixture stirred overnight at room temperature. The pH was brought to 4 by the addition of acetic acid, the excess of solvent removed on a rotary evaporator, potassium dihydrogenphosphate solution added (saturated) and the mixture extracted by ethyl acetate. After drying over sodium sulfate and removal of solvent, acid 9 was obtained (1.9 g, 93% yield). $^1$H NMR (CDCl$_3$-MeOH, 4:1): 1.27 (3H, s, H18); 1.38 (1H, d, $J_{17,17}$=7.3 Hz, H17); 1.70 (1H, d, $J_{17,17}$=7.3 Hz, HO17); 2.64 (1H, d, $J_{6,5}$=9.0 Hz, H5); 2.72 (1H, d, $J_{5,6}$=9.0 Hz, H6); 5.67 (1H, br d, J=9.2 Hz, H3); 5.79 (1H, d tr, J=9.2 Hz, J=3.0 Hz, H2)

EXAMPLE 9 ent-16β,17-Dichloromethano-13-hydroxy-20-norgibberell-2-ene-7,19-dioic Acid 19,10-Lactone 7-Methoxymethyl ester (10)

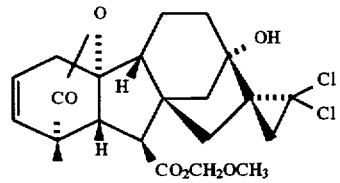

A solution of 13-hydroxy-20-norgibberell-2-ene-7,19-dioic Acid 19,10-Lactone (GA$_5$) (MacMillan et al., Tetrahedron, 1960, 11, 60) (194 mg, 0.59 mmol) in dichloromethane (10 ml) and triethylamine (250 μl, 0.18 mmol) was treated with methoxymethyl chloride (54 μl, 7.2 mmol) and the mixture stirred at room temperature for 15 min. Saturated sodium bicarbonate solution was added and the product extracted into ethylacetate. After drying over sodium sulfate, the solvent was removed and half of the residue (99 mg) dissolved in chloroform (3 ml). Powdered sodium hydroxide (0.4 g, 0.01 mol) was quickly added under an atmosphere of nitrogen, followed by benzyltriethylammonium chloride (6 mg) and stirring maintained for 8.5 h. The mixture was filtered through celite, washed with sodium dihydrogenphosphate solution (20%), dried over sodium sulfate, concentrated and chromatographed on silica, eluting with ethyl acetate/petroleum ether (40°–60° C.) (1:2) to afford the adduct 10 (81 mg, 67% yield) as a white foam. $^1$H NMR (CDCl$_3$): 1.28 (3H, s, H18); 1.42 (1H, d, $J_{17,17}$=7.3 Hz, H17); 1.73 (1H, d, $J_{17,17}$=7.3 Hz, HO17); 2.71 (1H, d, $J_{6,5}$=9.0 Hz, H5); 2.79 (1H, d, $J_{5,6}$=9.0 Hz, H6); 5.70 (1H, br d, J=9.2 Hz, H3); 5.82 (1H, d tr, J=9.2 Hz, J=3.0 Hz, H2)

EXAMPLE 10 ent-16β,17-Chloromethano-13-Hydroxy-20-norgibberell-2-ene-7,19-dioic Acid 19,10-Lactone 7-Methoxymethyl ester (11)

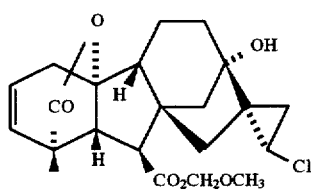

A solution of ester 10 (40 mg, 0.087 mmol) in benzene (2 ml) was treated with tri-n-butylstannane (26 μl, 0.096 mmol) and a crystal of AIBN. The mixture was heated at reflux under a nitrogen atmosphere for 1 hr. After removal of solvent, the residue was dissolved in ether and washed with aqueous ammonia (x 3). The dried organic layer was reduced to dryness and chromatographed on silica gel. The monochloro product 11 (35 mg, 95% yield, single epimer with unspecified configuration) was eluted with ethylacetate/hexane (1:2). $^1$H NMR (CDCl$_3$): 0.73 (1H, m, H17); 1.27 (1H, dd, J=6.6, 8.1 Hz, HO17); 1.28 (3H, s, H18); 2.69 (1H, d, $J_{6,5}$=9.0 Hz, H5); 2.81 (1H, d, $J_{5,6}$32 9.0 Hz, H6); 3.43 (1H, dd, J=8.1, 4.1 Hz, CHCl); 3.50 (3H, s, OMe); 5.28 (2H, s, OCH$_2$O); 5.69 (1H, br d, J=9.2 Hz, H3); 5.82 (1H, d tr, J=9.2 Hz, J=3.0 Hz, H2).

EXAMPLE 11 ent-16β,17-Chloromethano-13-hydroxy-20-norgibberell-2-ene-7,19-dioic Acid 19,10-Lactone (12)

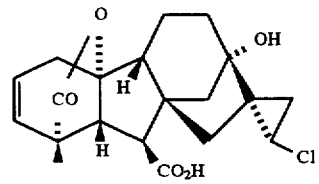

A solution of ester 11 (17 mg, 0.040 mmol) in dichloromethane (2 ml) was treated with trifluoroacetic acid (0.2 ml) and the mixture stirred at room temperature under a nitrogen atmosphere for 1 h. After removal of solvent, acid 12 was obtained as a colourless glass. $^1$H NMR (d$_8$-THF): 0.63 (1H, m, H17); 1.10 (1H, dd, J=6.6, 8.1 Hz, HO17); 1.18 (3H, s, H18); 2.53 (1H, d, $J_{6,5}$=9.1 Hz, H5); 2.71 (1H, d, $J_{5,6}$=9.1 Hz, H6); 3.37 (1H, dd, J=8.1, 4.1 Hz, CHCl); 5.65 (1H, br d, J=9.2 Hz, H3); 5.79 (1H, d tr, J=9.2 Hz, J=3.0 Hz, H2).

EXAMPLE 12 ent-3α-Acetoxy-16β,17-dibromomethano-13-hydroxy-20-norgibberell-1-ene-7,19-dioic Acid 19,10-Lactone 7-Methoxymethyl Ester (13)

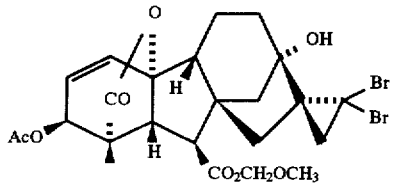

Sodium hydroxide solution 50%, 2 ml) was added to a solution of ester 3 (173 mg, 0.40 mmol), choline chloride (11 mg, 0.08 mmol) and bromoform (70 μl, 0.8 mmol) in dichloromethane (4 ml) under a nitrogen atmosphere, and the mixture stirred vigorously for 2.5 h. Further bromoform (50 μl) was added and stirring continued for 0.5 h. Ethyl acetate was added and the organic layer washed with water, then saturated brine. Chromatography on silica gel afforded the adduct 13 (103 mg, 43% yield). $^1$H NMR (CDCl$_3$): 1.19 (3H, s, H18); 1.65 (1H, d, $J_{17,17}$=7.6 Hz, H17); 2.02 (1H, d, $J_{17,17}$=7.6 Hz, HO17); 2.10 (3H, s, OCOCH$_3$); 2.84 (1H, d, $J_{6,5}$=10.5 Hz, H6); 3.34 (1H, d, $J_{5,6}$=10.5 Hz, H5); 3.54 (3H, s, CH$_2$OCH$_3$); 5.30, 5.38 (2H, ABd, J=6.1 Hz, CH$_2$OCH$_3$); 5.34 (1H, br s, H3); 5.89 (1H, dd, $J_{2,1}$=9.3 Hz, $J_{2,3}$=3.8 Hz, H2); 6.39 (1H, d, $J_1$=9.3 Hz, H1)

EXAMPLE 13 ent-16β,17-Dibromomethano-3α,13-dihydroxy-20-norgibberell-1-ene-7,19-dioic Acid 19,10-Lactone (14)

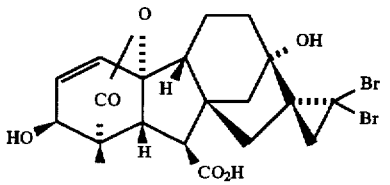

Trimethyl silyl chloride (40 μl) was added to a solution of ester 13 (20 mg) in tetrahydrofuran (2.0 ml) containing methanol (20 μl) and the solution stirred for 20 h. After dilution with ethyl acetate, the product was extracted into a pH 8.5 phosphate buffer (5×2 ml). The combined extracts were acidified to pH 6 with pH 4 phosphate buffer, and extracted with ethyl acetate/2-butanol (3x) to afford ent-3α-acetoxy-16β,17-dibromomethano-13-hydroxy-20-norgibberell-1-ene-7,19-dioic acid 19,10-lactone (18.3 mg), which was dissolved in methanol (1 ml) and treated with a solution of KHCO$_3$ (3.3 mg) and K$_2$CO$_3$ (9.1 mg) in water (0.50 ml). After stirring for 2 h, pH 4 phosphate buffer was added and the mixture extracted with ethyl acetate (2x). Drying and removal of solvent afforded the desired product 14 (17 mg). $^1$H NMR (CDCl$_3$-d$_4$-MeOH, 4:1): 1.19 (3H, s, H18); 1.58 (1H, d, $J_{17,17}$=7.4 Hz, H17); 1.94 (1H, d, $J_{17,17}$=7.4 Hz, HO17); 2.69 (1H, d, $J_{6,5}$=10.08 Hz, H6); 3.31 (1H, d, $J_{5,6}$=10.08 Hz, H5);4.0, (1H, d, J=3.6 Hz, H3); 5.82 (1H, dd, $J_{2,1}$=9.3 Hz, $J_{2,3}$=3.8 Hz, H2); 6.23 (1H, d, $J_1$=9.3 Hz, H1).

EXAMPLE 14 ent-3α-Acetoxy-13-hydroxy-16,17-methano-20-norgibberell-1-ene-7,19-dioic Acid 19,10-Lactone 7-Methoxymethyl Ester (15)

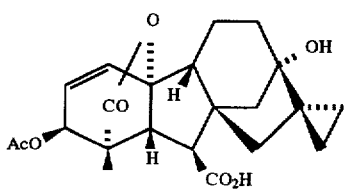

To a solution of ester 13 (120 mg, 0.2 mmol) in benzene (10 ml) was added tri-n-butylstannane (0.13 ml) and AIBN (one crystal). After stirring under a nitrogen atmosphere at reflux for 2 h, a further crystal of AIBN was added, and reflux maintained for 1 h. More tri-n-butylstannane (65 μl) was then added and the reaction continued for a further 2 h, at which point tlc indicated only a trace of starting material remained. The mixture was reduced to dryness (rotavap), the residue dissolved in ethyl acetate, and the solution washed with dilute ammonia (3x). After drying and concentration, the product was chromatographed on silica gel, eluting with ethyl acetate/hexane (1:2, then 1:1) to afford the debrominated ester 15 (63 mg, 71% yield). $^1$H NMR (CDCl$_3$): 0.32 (1H), 0.56 (2H), 0.89 (1H), (3xm, H16, H17); 1.17 (3H, s, H18); 2.11 (3H, s, OCOCH$_3$); 2.79 (1H, d, $J_{6,5}$=10.7 Hz, H6); 3.32 (1H, d, $J_{5,6}$=10.7 Hz, H5); 3.50 (3H, s, OCH$_2$OCH$_3$); 5.22, 5.33 (2H, ABd, J=6.1 Hz, OCH$_2$OCH$_3$); 5.34 (1H, s, H3); 5.88 (1H, dd, $J_{2,1}$=9.3 Hz, $J_{2,3}$=3.8 Hz, H2); 6.43 (1H, d, $J_1$=9.3 Hz, H1).

EXAMPLE 15 ent-3α-Acetoxy-13-hydroxy-16,17-methano-20-norgibberell-1-ene-7,19-dioic Acid 19,10-Lactone (16)

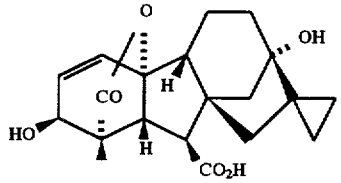

Hydrolysis of ester 15 as described for ester 13 (21 mg) afforded acid 16 (11 mg). $^1$H NMR (CDCl$_3$-d$_4$-MeOH, 4:1): 0.28 (1H), 0.49 (2H), 0.83 (1H), (3xm, H16, H17); 1.19 (3H, s, H18); 2.67 (1H, d, $J_{6,5}$=10.4 Hz, H6); 3.11 (1H, d, $J_{5,6}$=10.7 Hz, H5); 4.02 (1H, d, J=3.6 Hz); 5.84 (1H, dd, $J_{2,1}$=9.3 Hz, $J_{2,3}$=3.8 Hz, H2); 6.28 (1H, d, $J_1$=9.3 Hz, H1).

EXAMPLE 16 ent-13-Hydroxy-16,17-methano-20-norgibberell-2ene-7,19-dioic Acid 19,10-Lactone (17)

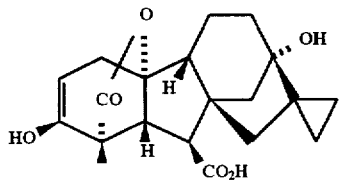

Diiodomethane (0.330 ml), iodine (52 mg) and copper powder (520mg) were added to a solution of $GA_5$ methyl ester (94 mg, prepared as described by (MacMillan et al., Tetrahedron, 1960, 11, 60) in toluene (5.0 ml), and the mixture heated at reflux under an atmosphere of nitrogen for 21 h. After filtering through celite with an ether wash, the solvent was removed and the residue chromatographed on silica gel. ent-13-Hydroxy-16,17-methano-20-norgibberell-2-ene-7,19-dioic Acid 19,10-lactone 7-methyl ester (62 mg, 63%) was eluted with ethyl acetate/hexane (1:2) and crystallised slowly from ethyl acetate. A suspension of this product (32.6 mg) in methanol (2.0 ml) was treated with 2N sodium hydroxide (2.0 ml) and the mixture heated under reflux for 15 h. The pH was lowered to 5 by the addition of 5N hydrochloric acid and the product extracted into ethyl acetate. After washing with brine, and drying over sodium sulfate, the solvent was removed and the residue dissolved in glacial acetic acid (0.5 ml). The solution was heated to 100° C. for 10 min., the solvent removed and the residue chromatographed on silica gel. Acid 17 was eluted with ethyl acetate/hexane (7:3) and obtained as a white solid (25.6 mg, 81% yield). $^1$H NMR (CDCl$_3$-d$_4$-MeOH, 4:1): 0.23 (1H), 0.46 (2H), 0.82 (1H), (3xm, H16, H17); 1.19 (3H, s, H18); 2.52 (1H, d, $J_{6,5}$=9.0 Hz, H5); 2.66 (1H, d $J_{5,6}$=9.0 Hz, H6); 5.61 (1H, br d, J=9.3 Hz, H3); 5.77 (1H, d tr, J=9.3 Hz, J=2.9 Hz, H2).

EXAMPLE 17 ent-13-Acetoxy-16,17-methano-3α-hydroxy-20-norgibberell-1-ene-7,19-dioicAcid 19,10-Lactone7-Methyl Ester (18, R=H)

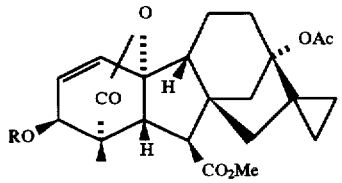

ent-3α,13-Diacetoxy-16β,17-dibromomethano-20-norgibberell-1-ene-7,19-dioic acid 19,10-lactone 7-methyl ester (260 mg, 0.42 mmol) was prepared in 45% yield from ent-3α,13-diacetoxy-20-norgibberella-1,16-diene-7,19-dioic acid 19,10-lactone 7-methyl ester (B. E. Cross, J Chem Soc., 1954, 4670) by the procedure described for the 3-acetate 13, and dissolved in benzene (10 ml). Tri-n-butylstannane (340 µl, 1.26 mmol) and AIBN (10 mg, 63 µmol) were added and the mixture heated at reflux under a nitrogen atmosphere for 3.5 h. Further stannane (350 µl) was added and the reflux continued for a further 18 h. The reaction mixture was diluted with ether, washed with dilute ammonia, brine, and dried over sodium sulfate. Chromatography on silica gel, eluting with ethyl acetate/hexane (1:3) afforded diacetate 18 (R=Ac) (74 mg). Elution with ethyl acetate/hexane (1:1) afforded the 13-monoacetate 18 (R=H) (64 mg). The diacetate was converted into the 13-monoacetate as described for the preparation of ester e, affording a further 89 mg of product 18 (R=H) (total yield for two steps, 51%). $^1$H NMR (CDCl$_3$): 0.38 (1H), 0.49 (1H), 0.80 (1H), 0.96 (1H), (4xm, H16, H17); 1.22 (3H, s, H18); 1.96 (3H, s, OCOCH$_3$); 2.79 (1H, d, $J_{6,5}$=10.7 Hz, H6); 3.19 (1H, d, $J_{5,6}$=10.7 Hz, H5); 3.70 (3H, s, CO$_2$Me); 4.15 (1H, m, H3); 5.92 (1H, dd, $J_{2,1}$=9.3 Hz, $J_{2,3}$=3.8 Hz, H2); 6.36 (1H, d, $J_1$=9.3 Hz, H1).

EXAMPLE 18 ent-13-Acetoxy 3α-hydroxy-16-methyl-20-norgibberellane-7, 19-dioic Acid 19,10-Lactone 7-Methyl Ester (19)

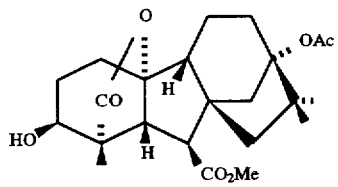

A solution of ester 18 (89 mg, 0.21 mmol) in ethyl acetate (5 ml) containing 5% Rh-Al$_2$O$_3$ (6 mg) was stirred at room temperature under an atmosphere of hydrogen for 22 h. A further sample of catalyst (6 mg) was added and the reaction continued for a further 50 h. After filtration, the solvent was removed and the residue dissolved in acetic acid (3 ml). Platinum oxide (10 mg) was added and the mixture stirred at 50° C. for 16 h under an atmosphere of hydrogen. The filtered (celite, dichloromethane washes) mixture was evaporated to dryness, and the residue chromatographed on silica gel, eluting with ethyl acetate/hexane (1:1). Ester 19 was obtained as a colourless solid (78 mg, 87% yield). $^1$H NMR (CDCl$_3$): 0.98 (3H, s, 16-Me); 1.11 (3H, s, 16-Me); 1.18 (3H, s, H18); 1.99 (3H, s, OCOCH$_3$); 2.63 (1H, d, $J_{6,5}$=11.0 Hz, H6); 3.14 (1H, d, $J_{5,6}$=11.0 Hz, H5); 3.72 (3H, s, CO$_2$Me); 3.82 (1H, br s, H3)

EXAMPLE 19 ent-13-Acetoxy-16-methyl-20-norgibberell-2-ene-7, 19-dioic Acid 19,10-Lactone 7-Methyl Ester (20)

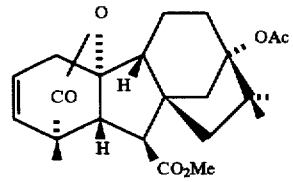

To a stirred solution of carbinol 19 (59 mg) in dry dichloromethane (3 ml) at 4° C. under a nitrogen atmosphere was added triethylamine (78 µl) followed by methanesulfonyl chloride (95 µl). After 1 h a piece of ice was added and the mixture stirred for 15 min. Further ice was then added, stirring continued for 10 min., and the temperature allowed to rise to ambient. The mixture was diluted with ethyl acetate, washed with potassium dihydrogenphosphate (20%), brine, potassium carbonate solution (10%), and dried over sodium sulfate. Removal of solvent afforded the crude 3-mesylate which was dissolved in toluene (3 ml, distilled from calcium hydride). DBU (105 µl) added, and the solution heated at 120° C. under an atmosphere of nitrogen for 12 h. The cooled solution was extracted with potassium carbonate solution, the extracts acidified with 1N HCl, and the product extracted into ethyl acetate. The organic layer was washed with water until neutral, dried (sodium sulfate) and reduced to dryness. The residue was chromatographed on silica gel and alkene 20 was eluted with ethyl acetate/hexane (3:1) (37 mg, 61% yield). $^1$H NMR (CDCl$_3$): 0.98 (3H, s, 16-Me); 1.18 (3H, s, 16-Me); 1.19 (3H, s, H18); 1.98 (3H, s, OCOCH$_3$); 2.36 (1H, d, $J_{6,5}$=9.4 Hz, H5); 2.73 (1H, d, $J_{5,6}$=10.5 Hz, H6); 3.72 (3H, s, OMe); 5.64 (1H, br d, J=9.3 Hz, H3); 5.83 (1H, d tr, J=9.3 Hz, J=2.9 Hz, H2).

EXAMPLE 20 ent-3α,13-Dihydroxy-16-methyl-20-norgibberell-2-ene-7,19-dioic Acid 19,10-Lactone (21)

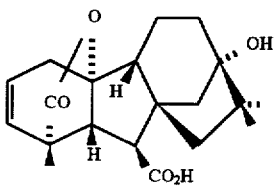

A suspension of ester 20 (30 mg) in methanol (2.0 ml) was treated with 2N sodium hydroxide (2.0 ml) and the mixture heated under reflux for 15 h. The pH was lowered to 5 by the addition of 5N hydrochloric acid and the product extracted into ethyl acetate. After washing with brine, and drying over sodium sulfate, the solvent was removed and the residue dissolved in glacial acetic acid (0.5 ml). The solution was heated to 100° C. for 10 min., the solvent removed and the residue chromatographed on silica gel. Acid 21 was eluted with ethyl acetate/hexane (7:3) and obtained as a white solid (23 mg, 80% yield). $^1$H NMR (d$_4$-MeOH): 1.05 (3H, s, 16-Me); 1.08 (3H, s, 16-Me); 1.24 (3H, s, H18); 2.50 (1H, d, $J_{6,5}$=9.3 Hz, H5); 2.72 (1H, d, $J_{5,6}$=9.3 Hz, H6); 5.74 (1H, br d, J=9.3 Hz, H3); 5.90 (1H, d tr, J=9.3 Hz, J=2.9 Hz, H2).

EXAMPLE 21 ent-16β,17-dichloromethano-3α,13-dihydroxy-20-norgibberell-1ene-7,19-dioic Acid 19,10-Lactone (22)

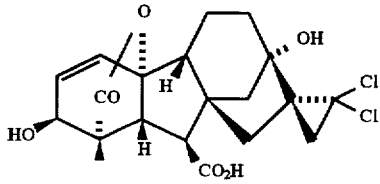

Acetoxy ester 4 (50 mg) was hydrolysed to acid 22 in 72% yield as described for ester 14. $^1$H NMR (CDCl$_3$): 1.24 (3H, s, H18); 1.39 (1H, d, $J_{17,17}$=7.5 Hz, H17); 1.71 (1H, d, $J_{17,17}$=7.5 Hz, HO17); 2.75 (1H, d, $J_{6,5}$=10.5 Hz, H6); 3.13 (1H, d, $J_{5,6}$=10.5 Hz, H5); 4.09 (1H, d, J=3.6 Hz, H3); 5.87 (1H, dd, $J_{2,1}$=9.3 Hz, $J_{2,3}$=3.8 Hz, H2); 6.28 (1H, d, $J_1$=9.3 Hz, H1).

EXAMPLE 22 ent-16β,17-Chloromethano-3α,13-dihydroxy-20-norgibberell-1-ene-7,19-dioic Acid 19,10-Lactone (23)

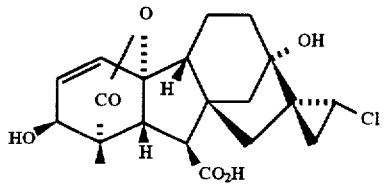

Acetoxy ester 4 (65 mg) was monodechlorinated in 75% yield as described for the preparation of ester 11, then hydrolysed to acid 23 in 83% yield as described for ester 14. $^1$H NMR (CDCl$_3$): 0.69 (1H, m, H17); 1.14 (1H, dd, J=6.6, 8.1 Hz, HO17); 1.24 (3H, s, H18); 2.74 (1H, d, $J_{6,5}$=10.5 Hz, H6); 3.15 (1H, d, $J_{5,6}$=10.5 Hz, H5); 4.07 (1H, d, J=3.6 Hz, H3); 5.88 (1H, dd, $J_{2,1}$=9.3 Hz, $J_{2,3}$=3.8 Hz, H2); 6.30 (1H, d, $J_1$=9.3 Hz, H1)

EXAMPLE 23 ent-16β,17-Bromomethano-3α,13-dihydroxy-20-norgibberell-1-ene-7,19-dioic Acid 19,10-Lactone (24)

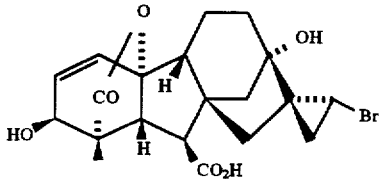

To a solution of ester 13 (120 mg, 0.2 mmol) in benzene (5 ml) was added tri-n-butylstannane (0.065 ml, 86% purity, 0.21 mmol) and AIBN (one crystal). After stirring under a nitrogen atmosphere at room temperature for 5 h, the mixture was reduced to dryness (rotavap), the residue dissolved in ether, and the solution washed with dilute ammonia (3x). After drying and concentration, the product was chromatographed on silica gel, eluting with ethyl acetate/hexane (1:2, then 1:1) to afford the monodebrominated ester as a single epimer of unspecified configuration (74 mg, 71% yield). A portion of this product (20 mg) was hydrolysed to acid 24 in 62% yield as described for ester 14. $^1$H NMR (CDCl$_3$-d$_4$-MeOH, 4:1): 0.72 (1H, dd, J=4.6 Hz, 7.5 Hz, H17); 1.18 (3H, s, H18); 2.69 (1H, d, $J_{6,5}$=10.5 Hz, H6); 3.12 (1H, d, $J_{5,6}$=10.5 Hz, H5); 3.30 (1H, dd, J=4.5 Hz, 6.3 Hz, CHBr); 4.0, (1H, d, J=3.6 Hz, H3); 5.82 (1H, dd, $J_{2,1}$=9.3 Hz, $J_{2,3}$=3.8 Hz, H2); 6.24 (1H, d, $J_1$=9.3 Hz, H1).

EXAMPLE 24 ent-3α,13-Diacetoxy-10β-hydroxy-16β,17-epoxy-20-norgibberell-1-ene-7,19-dioic Acid 7-Methoxymethyl Ester 19,10-Lactone (25)

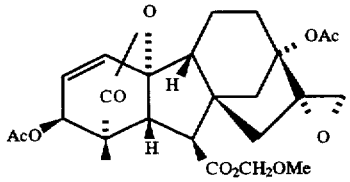

The water was removed from a solution of m-chloroperbenzoic acid (28 g, 60% stabilized with water, 0.1 mol) in dichloromethane (350 ml), followed by drying over sodium sulfate. The dichloromethane solution was then added to a solution of the of the 3,13-diacetate of giberrellic acid methoxymethyl ester (35 g, 0.0788 mol) in dry dichloromethane (500 ml) with stirring under a nitrogen atmosphere at −15° C. The mixture was then allowed to warm slowly to 4° C. and was kept at this temperature. After 4 days, saturated sodium bicarbonate solution (150 ml) was added and the reaction left to stir for 1.5 h. The layers were separated and the aqueous phase was extracted with dichloromethane (2×50 ml). The combined organic phases were dried over sodium sulfate, filtered, and the solvent removed in vacuo. The oily residue was passed through a short plug of silica gel (dichloromethane). The solvent was removed and the residue was recrystallized (hexane/ethyl acetate, 2:1, 180 ml), to yield the desired α-epoxide 25 (29.1 g, 80%).

EXAMPLE 25 ent-3α,13-Diacetoxy-10β-hydroxy-17-oxo-20-nor-16ζ-gibberell-1-ene-7,19-dioic Acid 7-Methoxymethyl Ester 19,10-Lactone (26)

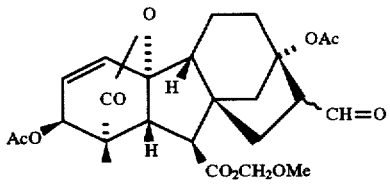

Zinc powder (4.2 g, 0.064 mol) was added to a solution of titanocene dichloride (15 g, 0.06 mol) in dry THF (400 ml) stirring under a nitrogen atmosphere. After 2 h of stirring at room temperature the reaction mixture was cooled to −15° C. and epoxide (25) (6.1 g 0.013 mol) dissolved in dry THF (150 ml) was cannulated into the reaction mixture. The reaction was warmed up to room temperature and was left stirring for 1 h then cooled to 0° C. and sulfuric acid (10%, 100 ml) added. The reaction mixture was diluted with ether (500 ml) and the acid was neutralised with solid sodium bicarbonate. The layers were separated and the aqueous layer was extracted with ether (2×100 ml). The combined organic phases were washed with brine (2×200 ml), dried over sodium sulfate, filtered, and the solvent removed in vacuo. Purification of the residue on silical gel (hexane/ethyl acetate, 3:1–1:1) provided aldehyde (26) as a 5:3 mixture of 16β and 16α-epimers (3.2 g, 56% yield). $^1$H NMR δ9.64 (d, J=2.5 Hz, 16α-CH=O) and 10.02 (s, 16β-CH=O).

EXAMPLE 26 ent-3α,13-Diacetoxy-10β-hydroxy-17-methylene-20-nor-16ζ-gibberell-1-ene-7,19-dioic Acid 7-Methoxymethyl Ester 19,10-Lactone (27)

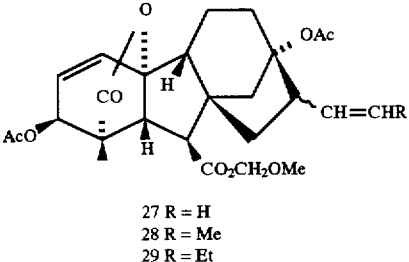

27 R = H
28 R = Me
29 R = Et

A suspension of sodium hydride (1.12 g, 60%) in mineral oil was washed with petroleum ether and added to a suspension of methyl triphenyl phosphonium bromide in tetrahydrofuran and the mixture heated at reflux for 2 h. After cooling, the resulting yellow solution was added in portions to a solution of aldehyde epimers (26) (2.75 g) in THF (16 ml) with stirring at −78° C. until the yellow colour persisted in the reaction mixture. The mixture was allowed to warm to room temperature gradually and then to stir for 18 h. Excess solvent was removed under reduced pressure and the residue chromatographed on silica gel. The ethene adduct 27 was eluted with 10% ethyl acetate in pentane affording 1.23 g (45% yield).

Following the procedure outlined above, the ylide generated from ethyl triphenyl phosphonium iodide was added to aldehyde (26), affording the propene analogue ent-3α,13-Diacetoxy-10β-hydroxy-17-ethylidene-20-nor-16ζ-gibberell-1-ene-7,19-dioic Acid 7-Methoxy-methyl Ester 19,10-Lactone (28) in 37% yield, while the ylide generated from n-propyl triphenyl phosphonium iodide afforded the butene analogue ent-3α,13-Diacetoxy-10β-hydroxy-17-propylidene-20-nor-16ζ-gibberell-1-ene-7,19-dioic Acid 7-Methoxy-methyl Ester 19,10-Lactone (29) in 53% yield.

EXAMPLE 27 ent-13-Acetoxy-10β-hydroxy-17-methyl-20-nor-16ζ-gibberell-2-ene-7,19-dioic Acid 7-Methoxymethyl Ester 19,10-Lactone (30)

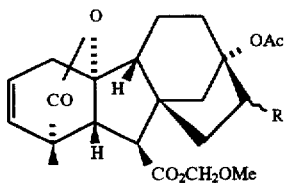

30 R = Et
31 R = nPr
32 R = nBu

Diene (27) (1.23 g) was dissolved in methanol (12.5 ml) and treated with a solution of potassium carbonate (23%, 2.5 ml) and the mixture stirred for 30 minutes. The mixture was brought to pH 5.5 with acetic acid, reduced to dryness and the residue extracted into ethyl acetate. This extract was washed with water, potassium carbonate solution, brine, and dried over sodium sulfate. After removal of solvent, the residue was redissolved in ethyl acetate, the solution degassed, 5% rhodium-alumina (112 mg) added and the suspension stirred under a hydrogen atmosphere for 17 h. After filtration through Celite to remove the catalyst, the solution was reduced to dryness, the residue dissolved in dry THF, triphenyl phosphine (759 mg) added, followed by diethyl azodicarboxylate (504 mg) and the resulting mixture heated under reflux for 20 minutes. The mixture was then concentrated and the residue chromatographed on silica gel. The GA$_5$ analog (30) was eluted with mixtures of 10% and 20% ethyl acetate in hexane. A total of 701 mg (69%) yield was obtained over three steps. Repetition of this procedure utilising the propene substrate (28) afforded the GA$_5$ analog (31) (72% yield over three steps), while the butene substrate (29) afforded the GA$_5$ analog (32) (64% yield over three steps).

EXAMPLE 28 ent-13-Acetoxy-10β-hydroxy-17-methyl-20-norgibberell-2-ene-7,19-dioic Acid 19,10-Lactone (33b) and the 16-epimer (33a)

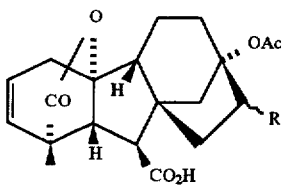

33a R = 16α-Et    33b R = 16β-Et
34a R = 16α-nPr   34b R = 16β-nPr
35a R = 16α-nBu   35b R = 16β-nBu

Dowex W50×2 (H$^+$) resin was added to the ester (30) (701 mg) suspended in methanol (6.75 ml)-water (1.35 ml) and the mixture heated under reflux for 1 h. After filtration of the resin, the solvent was removed and the 16-epimers (33a) and (33b) separated by preparative HPLC on a C$_{18}$ reverse phase column (Waters Nova-Pak HR C18 6 micron), eluting with water-methanol (70:30, containing 0.05% acetic acid) and characterised by NMR spectra. 33a (16α-ethyl) was eluted first: $^1$H NMR (CDCl$_3$/d$_4$-MeOH, 4:1) δ0.76 (3H, t, J=7.3 Hz, CH$_2$CH$_3$), 1.22 (3H, s, H-18), 2.00 (3H, s, OAc), 2.32, 2.58 (2×1H, ABd, J=16.1 Hz, H-1), 2.67, 2.72 (1H, ABd, J=9.4 Hz, H-5, 6), 5.65 (1H, br d, J=6.4 Hz, H-3), 5.70 (1H, dt, J=6.4, 3.5 Hz, H-2). 33b (16β-ethyl): $^1$H NMR (CDCl$_3$/d$_4$-MeOH, 4:1) δ0.87 (3H, t, J=7.3 Hz, CH$_2$CH$_3$), 1.22 (3H, s, H-18), 1.96 (3H, s, OAc), 2.32, 2.57 (2×1H, ABd, J=16.1 Hz, H-1), 2.63, 2.71 (1H, ABd, J=9.4 Hz, H-5, 6), 5.64 (1H, br d, J=6.4 Hz, H-3), 5.78 (1H, dt, J=6.4, 3.5 Hz, H-2). $^{13}$C NMR (CDCl$_3$) δ12.9, 15.3, 17.1, 22.1, 24.1, 26.2 (C-12), 35.3, 40.4, 42.2, 47.9, 48.2, 51.6, 55.1, 56.9, 85.8, 91.4, 127.7, 132.1, 170.4, 177.5.

EXAMPLE 29 ent-10β,13-Dihydroxy-17-methyl-20-nor-16-epi-gibberell-2-ene-7,19-dioic Acid 19,10-Lactone (36a)

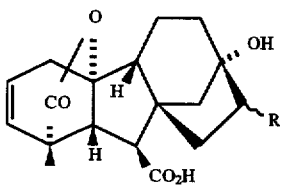

36a R = 16α-Et    36b R = 16β-Et
37a R = 16α-nPr   37b R = 16β-nPr
38a R = 16α-nBu   38b R = 16β-nBu

Potassium hydroxide (120 mg) was added to a solution of acetate (33a) (60 mg) and the mixture heated at reflux under a nitrogen atmosphere for 2 h. The pH was brought to 5.5 with acetic acid and reduced to dryness. The product was extracted into ethyl acetate and after washing with brine, then drying over sodium sulphate, chromatographed on silica gel. Acid (36a) (16α-ethyl) was eluted with ethyl acetate/dichloro methane/hexane (3:1:6) containing 0.5% acetic acid. $^1$H NMR (CDCl$_3$/d$_4$-MeOH, 4:1) δ0.75 (3H, t, J=7.3 Hz, CH$_2$CH$_3$), 1.22 (3H, s, H-18), 2.26, 2.52 (2×1H, ABd, J=16.1 Hz, H-1), 2.48, 2.65 (1H, ABd, J=9.3 Hz, H-5, 6), 5.58 (1H, br d, J=6.4 Hz, H-3), 5.73 (1H, dt, J=6.4, 3.5 Hz, H-2). $^{13}$C NMR (CDCl$_3$/d$_4$-MeOH, 4:1) δ11.8, 14.9, 17.1, 24.8, 34.9, 39.6 (C-12), 42.8, 43.8, 47.5, 51.0, 52.3, 55.5, 77.4, 92.37, 127.7, 132.3, 174.3, 178.7.

The analogs (36b), (37a), (37b), (38a), and (38b) were similarly prepared and were characterised by their NMR spectra. Typically, the 16α (exo)-epimers were eluted before the 16β (endo) epimers, while all six compounds displayed resonances in NMR spectra associated with the C-4 methyl group at approximately δ1.24; with the ring-A double bond at approximately δ5.65 (br d, J=6.4 Hz, H-3) and 5.77 (dt, J=6.4, 3.5 Hz, H-2), δ127.8 (C-3) and 132.1 (C-2); with H-5 and H-6 at approximately δ2.57 and 2.70 (ABd, J=9.4 Hz); with H, H'-1 at approximately δ2.32 and 2.38 (ABd, J=16 Hz). The terminal methyl group for each of the side chains was observed as a triplet (J=7.3 Hz) in the range 0.6 to 0.9 ppm. For each pair of epimers, the $^1$H resonance associated with the terminal methyl group in the side chain occurred at a smaller frequency for the 16α (exo) epimer relative to the 16β (endo) epimer. Also, for each pair of epimers, the $^{13}$C resonance associated with C-12 was observed at a higher frequency for the 16β (exo) epimer (ca. 37-39 ppm) relative to the 16β (endo) epimer (ca. 26-30 ppm).

ent-10β,13-Dihydroxy-17-methyl-20-norgibberell-2-ene-7, 19-dioicAcid19,10-Lactone (36b) (16β-ethyl): $^1$H NMR (CDCl$_3$/d$_4$-MeOH, 4:1) δ0.81 (3H, t, J=7.3 Hz, CH$_2$CH$_3$), 1.16 (3H, s, H-18), 2.26, 2.47 (2×1H, ABd, J=16.1 Hz, H-1), 2.48, 2.65 (1H, ABd, J=9.3 Hz, H-5, 6), 5.57 (1H, br d, J=6.4 Hz, H-3), 5.72 (1H, dt, J=6.4, 3.5 Hz, H-2). $^{13}$C NMR (CDCl$_3$/d$_4$-MeOH, 4:1) δ12.9, 15.3, 17.1, 22.1, 24.1, 26.2 (C-12), 35.3, 40.4, 42.3, 47.9, 48.2, 51.6, 55.1, 56.9, 85.8, 91.4, 127.7, 132.1, 170.1, 177.5.

ent-10α,13-Dihydroxy-17-ethyl-20-nor-16-epi-gibberell-2-ene-7,19-dioic Acid 19,10-Lactone (37a) (16α-n-propyl): 0.79 (3H, t, J=7.3 Hz, CH$_2$CH$_2$CH$_3$), 1.17 (3H, s, H-18), 2.26, 2.52 (2×1H, ABd, J=16.1 Hz, H-1), 2.55, 2.69 (1H, ABd, J=9.4 Hz, H-5, 6), 5.63 (1H, br d, J=6.4 Hz, H-3), 5.74 (1H, dt, J=6.4, 3.5 Hz, H-2). $^{13}$C NMR (CDCl$_3$/d$_4$-MeOH, 4:1) δ14.1, 15.0, 17.2, 20.6, 34.3, 35.1, 39.7 (C-12), 43.2, 44.1, 45.3, 48.0, 50.9, 52.5, 55.6, 92.2, 127.8, 132.5, 174.7, 178.4.

ent-10β,13-Dihydroxy-17-ethyl-20-norgibberell-2-ene-7, 19-dioic Acid 19,10-Lactone (37b) (16β-n-propyl): 0.87 (3H, t, J=7.3 Hz, CH$_2$CH$_2$CH$_3$), 1.22 (3H, s, H-18), 2.29, 2.55 (2×1H, ABd, J=16.1 Hz, H-1), 2.57, 2.70 (1H, ABd, J=9.4 Hz, H-5, 6), 5.65 (1H, br d, J=6.4 Hz, H-3), 5.77 (1H, dt, J=6.4, 3.5 Hz, H-2). $^{13}$C NMR (CDCl$_3$/d$_4$-MeOH, 4:1) δ14.4, 15.3, 16.9, 22.0, 30.4 (C-12), 33.4, 35.2, 41.9, 46.7, 46.9, 48.2, 51.9, 52.0, 55.4, 55.6, 78.8, 91.9, 127.7, 132.4, 175.6, 177.9.

ent-10β,13-Dihydroxy-17-n-propyl-20-nor-16-epi-gibberell-2-ene-7,19-dioic Acid 19,10-Lactone (38a) (16α-n-butyl): 0.84 (3H, t, J=7.3 Hz, CH$_2$CH$_2$CH$_2$CH$_3$), 1.23 (3H, s, H-18), 2.32, 2.54 (2×1H, ABd, J=16.1 Hz, H-1), 2.57, 2.70 (1H, ABd, J=9.4 Hz, H-5, 6), 5.65 (1H, br d, J=6.4 Hz, H-3), 5.77 (1H, dt, J=6.4, 3.5 Hz, H-2). $^{13}$C NMR (CDCl$_3$/d$_4$-MeOH, 4:1) δ (13-OAc) 14.0, 15.3, 17.4, 21.7, 22.6, 29.2, 32.1, 35.3, 37.3 (C-12), 40.0, 42.5, 46.4, 48.1, 50.0, 51.5, 54.7, 55.0, 85.3, 91.5, 127.8, 132.1, 170.5, 177.0, 177.5.

ent-10β,13-Dihydroxy-17-n-propyl-20-norgibberell-2-ene-7,19-dioic Acid 19,10-Lactone (38b) (16β-n-butyl): 0.86 (3H, t, J=7.3 Hz, CH₂CH₂CH₂CH₃), 1.22 (3H, s, H-18), 2.33, 2.52 (2×1H, ABd, J=16.1 Hz, H-1), 2.57, 2.70 (1H, ABd, J=9.4 Hz, H-5, 6), 5.65 (1H, br d, J=6.4 Hz, H-3), 5.78 (1H, dt, J=6.4, 3.5 Hz, H-2). ¹³C NMR (CDCl₃/d₄-MeOH, 4:1) δ (13-OAc) 14.0, 15.3, 17.1, 22.1, 23.0, 26.2 (C-12), 30.6, 31.0, 35.3, 40.8, 42.2, 46.1, 48.2, 51.7, 55.1, 56.9, 85.8, 91.5, 127.7, 132.1, 170.4, 177.5.

EXAMPLE 30 ent-3α-Acetoxy-10β,13-dihydroxy-20-norgibberell-1-ene-7,19-dioic Acid 7-Methoxymethyl Ester 19,10-Lactone (3)

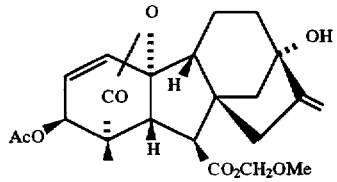

Gibberellic acid (GA₃) (250 g, 722 mmol) was suspended in dichloromethane (DCM) (1095 ml AR) under an atmosphere of dry nitrogen. The suspension was cooled in an ice/salt bath and triethylamine (115.7 ml, 1.15 equiv) added dropwise with overhead stirring. Methoxymethyl (MOM) chloride (63 ml, 1.15 equiv) was then added dropwise and the resulting mixture was stirred at rt for 45 min. TLC showed the presence of some starting material so triethylamine (7 ml, 0.07 equiv) and then further MOM chloride (3.8 ml, 0.07 equiv) was added and after a further 10 min, TLC showed only a faint trace of starting material.

The mixture was cooled in an ice/salt bath and triethylamine (503 ml, 5 equiv) was added dropwise with overhead stirring, a precipitate formed. Acetic anhydride (340.5 ml, 5 equiv) was then added dropwise and the mixture allowed to warm to rt and stirred (magnetically) for 16 h. The mixture was cooled in an ice/salt bath and water (100 ml) added gradually over 90 min with overhead stirring. The mixture was evaporated to about half its volume and diluted with ethyl acetate (700 ml), DCM (700 ml) and water (350 ml). The layers were separated and the aqueous layer extracted with ethyl acetate (3×100 ml). The combined organic layers were washed with ice cold 1N HCl (3×170 ml), water (6×200 ml), K₂CO₃ (2%, 3×170 ml then 24%, 2×120 ml), water (2×200 neutrality), brine (2×100 ml). The organic layer was dried (Na₂SO₄) and evaporated to give (3) as a crystalline solid (297.36 g, 95%). ¹H NMR: 1.16 (3H, s, H18); 2.10 (3H, s, OCOCH₃); 2.79 (1H, d, J₆,₅=10.9 Hz, H6);3.33 (1H, d, J₅,₆=10.9 Hz, H5); 3.47 (3H, s, CO₂CH₂OCH₃); 4.96 (1H, s, H17); 5.26 (1H, d, J=5.4 Hz CO₂CH₂OCH₃); 5.27 (1H, S, H17); 5.29 (1H, d, J=6.1 Hz, CO₂CH₂OCH₃); 5.33 (1H, d, J₃,₂=3.8 Hz, H3); 6.38 (1H, d, J₁,₂=9.3 Hz, H1)

EXAMPLE 31 ent-3α-Acetoxy-16β,17-dichloromethano-10β,13-dihydroxy-20-norgibberell-1-ene-7,19-dioic Acid 7-Methoxymethyl Ester 19,10-Lactone (4)

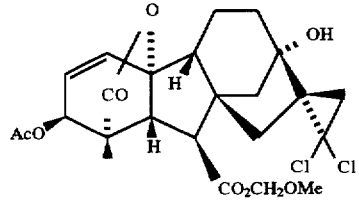

The protected gibberellin (3) prepared above (100 g, 231 mmol) was dissolved in chloroform (2310 ml) and to the efficiently stirred solution under an atmosphere of dry nitrogen was added powdered sodium hydroxide (87.49 g, 9.47 equiv) and a solution of benzyltriethylammonium chloride (859 mg, 2 mol %) in chloroform (10 ml) was added gradually. Intermittent ice cooling was employed to maintain the temperature below 30° C. After 2 h, powdered sodium hydroxide (30.88 g, 3.34 equiv) was added and a solution of benzyltriethylammonium chloride (PTC) (429 mg, 1 mol %) in chloroform (5 ml) was added gradually. At 3 h, powdered sodium hydroxide (27.34 g, 2.95 equiv) and a solution of benzyltriethylammonium chloride (429 mg, 1 mol %) in chloroform (5 ml) was added. After 3.5 h, TLC indicated that the reaction had gone to approximately 95% conversion so the mixture was filtered off through a sinter funnel and the filter cake washed with chloroform (400 ml). The filtrate was washed with KH₂PO₄ (20%,2×80 ml), brine (100 ml) dried (Na₂SO₄) and evaporated to give the crude reaction mixture. The oil obtained was purified by column chromatography on silica using 25% ethyl acetate in light petroleum (40°–60°) as the eluent increased to 50% ethyl acetate as the eluent. This furnished the desired product (4) as a foam (80.44 g, 75%; for 90% conversion). ¹H NMR: 1.17 (3H, s, H18); 1.39 (1H, d, J₁₇,₁₇=7.5 Hz, H17); 1.74 (1H, d, J₁₇,₁₇=7.5 Hz, HO17); 2.09 (3H, s, OCOCH₃); 2.81 (1H, d, J₆,₅=10.5 Hz, H6); 3.31 (1H, d, J₅,₆=10.5 Hz, H5); 3.52 (3H, s, CO₂CH₂OCH₃); 5.28 (1H, d, J=6.1 Hz, CO₂CH₂OCH₃); 5.33 (1H, d, J=6.1 Hz, CO₂CH₂OCH₃); 5.34 (1H, s, H3); 5.88 (1H, dd, J₂,₁=9.3 Hz, J₂,₃=3.8 Hz, H2); 6.39 (1H, d, J₁=9.3 Hz, H1)

EXAMPLE 32 ent-16β,17-dichloromethano-3α,10β-dihydroxy-20-norgibberell-1-ene-7,19-dioic Acid 7-Methoxymethyl Ester 19,10-Lactone (4a)

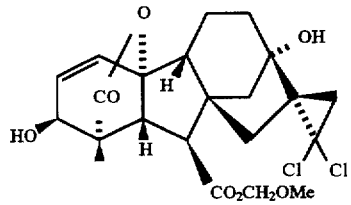

The cyclopropanated derivative (4) prepared above (156.7 g, 304 mmol) was dissolved in methanol (giving a suspension) and an aqueous carbonate solution (7.21 g K₂CO₃, 64.76 g KHCO₃ in water 313 ml; pH 8.5) added in three equal portions at 10 min intervals causing a precipitate to form. After a total reaction time of 50 min, the reaction had gone to completion by TLC. Acetic acid (53 ml, 3.05 equiv) was added and the mixture stirred until gas evolution ceased (at which time the pH was 5.5). The methanol was evaporated and the residue taken up in ethyl acetate (500 ml) and water (200 ml). The organic layer was separated and the aqueous layer extracted with ethyl acetate (3×100 ml). The combined organic layers were washed with aqueous $K_2CO_3$ (10%, 3×150 ml), brine (2×80 ml), dried ($Na_2SO_4$) and evaporated to give the 3,13-diol (4a) as a foam in quantitative yield. $^1H$ NMR: 1.22 (3H, s, H18); 1.39 (1H, d, $J_{17,17}$=7.5 Hz, H17); 1.69 (1H, d, $J_{17,17}$=7.5 Hz, HO17); 2.80 (1H, d, $J_{6,5}$=10.5 Hz, H6); 3.18 (1H, d, $J_{5,6}$=10.5 Hz, H5); 3.50 (3H, s, $CO_2CH_2OCH_3$); 4.12 (1H, br s, H3); 5.28 (2H, s $CO_2CH_2OCH_3$); 5.88 (1H, dd, $J_{2,1}$=9.3 Hz, $J_{2,3}$=3.8 Hz, H2); 6.30 (1H, d, $J_1$=9.3 Hz, H1).

EXAMPLE 33 ent-16β,17-Dichloromethano-3α,10β-dihydroxy-20-norgibberellane-7,19-dioic Acid 7-Methoxymethyl Ester 19,10-Lactone (4b)

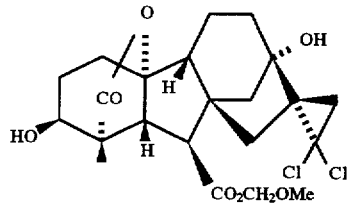

The starting material (4a) from the above reaction (114 mmol) was dissolved in ethyl acetate (380 ml) and the solution degassed. Rhodium on alumina catalyst (5% Rh, 5.63 g, 10% w/w) was added and the suspension saturated with hydrogen. The mixture was stirred under a balloon of hydrogen for 48 h and was found to be complete by proton nmr. Some product had crystallised out so DCM (300 ml) was added to dissolve this and the mixture allowed to settle before being decanted. The solution was filtered through a pad of celite and evaporated. The resulting solid was taken up in ethyl acetate (80 ml) and the product filtered off. The filtrate was evaporated and chromatographed on silica using 25% ethyl acetate in light petroleum (40°–60°) increased to 35% and then 40% ethyl acetate as the eluent. This gave the desired product (4b) (25.95 g crystallised and 17.74 g chromatographed; 81%). $^1H$ NMR: 1.18 (3H, s, H18); 1.39 (1H, d, $J_{17,17}$=7.5 Hz, HO17); 1.70 (1H, d, $J_{17,17}$=7.5 Hz, H17); 2.72 (1H, d, $J_{6,5}$=10.5 Hz, H6); 3.20 (1H, d, $J_{5,6}$=10.5 Hz, H5); 3.48 (3H, s, $CO_2CH_2OCH_3$); 3.83 (1H, br s, H3); 5.27,5.28 (2H, ABd, J=&.3 Hz $CO_2CH_2OCH_3$).

EXAMPLE 34 ent-16β,17-Dichloromethano-10β,13-dihydroxy-20-norgibberell-2-ene-7,19-dioic Acid 7-Methoxymethyl Ester 19,10-Lactone (10)

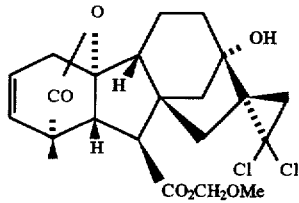

The 3-hydroxy derivative 4b prepared above (61.15 g, 129 mmol) and triphenylphosphine (37.11 g, 1.1 equiv) were dissolved in dry THF (430 ml). Diethyl azodicarboxylate (22.3 ml, 1.1 equiv) was added and the mixture heated to reflux. The mixture darkens considerably and was complete by TLC after approximately 25 min. The solution was allowed to cool and evaporated to half its volume. Silica (150 g) was added and evaporation continued to preadsorb the reaction mixture onto the silica. The preadsorbed residue was placed onto a pad of silica and eluted with 15% ethyl acetate in light petroleum (40°–60°) increased to 30% ethyl acetate and finally 35% ethyl acetate as the eluent. This gave the product (10) (contaminated with several minor impurities) which was used in the final deprotection without further purification.

EXAMPLE 35 ent-16β,17-Dichloromethano-3α,10β-dihydroxy-20-norgibberell-2-ene-7,19-dioic Acid 19,10-Lactone (9)

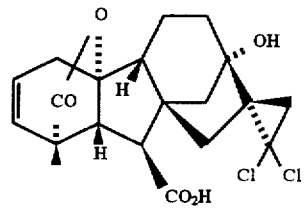

The crude product (10) from the elimination step (129 mmol) was dissolved in methanol (360 ml) and Dowex W50×2 $H^+$ form (43.66 g, 74% w/w) added. Water (72 ml) was added and the mixture heated at reflux for 2.5 h. At this time, TLC indicated that the reaction had gone to completion. The mixture was allowed to cool and the resin filtered off. The solution was evaporated to remove the methanol and ethyl acetate (300 ml) added. The suspension was washed with aqueous $K_2CO_3$ (10%, 3×130 ml) and the aqueous layer extracted with ethyl acetate (3×30 ml). The aqueous layer was carefully acidified with conc. HCl until the pH was 3, at which point a precipitate had formed. The solid was filtered off and washed to neutrality providing the desired product with no need for further purification (28.3 g, 53% over 2 steps). The aqueous layer was extracted with butan-2-ol (3×70 ml) and the organic layer washed with $KH_2PO_4$ (20%, 2×50 ml), brine (2×50 ml), dried ($Na_2SO_4$) and evaporated to give impure product which was chromatographed. The bulk of the product was obtained from filtration and a little more from the extraction. $^1H$ NMR ($CDCl_3$-MeOH, 4:1): 1.27 (3H, s, H18); 1.38 (1H, d, $J_{17,17}$=7.3 Hz, H17); 1.70 (1H, d, $J_{17,17}$=7.3 Hz, HO17); 2.64 (1H, d, $J_{6,5}$=9.0 Hz, H6); 2.72 (1H, d, $J_{5,6}$=9.0 Hz, H5); 5.67 (1H, br d, J=9.2 Hz, H3); 5.79 (1H, d tr, J=9.2 Hz, J=3.0 Hz, H2).

EXAMPLE 36 ent-16β,17-Dichloromethano-10β,13-dihydroxy-20-norgibberellane-7,19-dioic Acid 19,10-Lactone (9a)

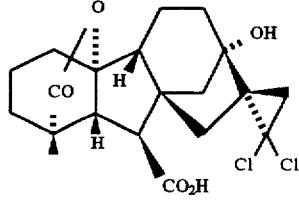

A solution of dichloromethano $GA_5$ (10) (2.0 g) in ethyl acetate (50 ml) containing rhodium-alumina (5%, 50 mg)

was stirred under an atmosphere of hydrogen for 16 h. After filtration to remove the catalyst, the solvent was removed to reveal the dichloromethano $GA_{20}$ derivative (9a) (2.0 g). $^1H$ NMR ($CDCl_3$-MeOH, 4:1): 1.12 (3H, s, H18); 1.38 (1H, d, $J_{17,17}$=7.3 Hz, H17); 1.70 (1H, d, $J_{17,17}$=7.3 Hz, HO17); 2.46 (1H, d, $J_{6,5}$=9.0 Hz, H5); 2.70 (1H, d, $J_{5,6}$=9.0 Hz, H6).

EXAMPLE 37 ent-3α,13-Diacetoxy-10β-hydroxy-17-methyl-17-oxo-20-norgibberell-1-ene-7,19-dioic Acid 7-Methoxymethyl Ester 19,10-Lactone (39)

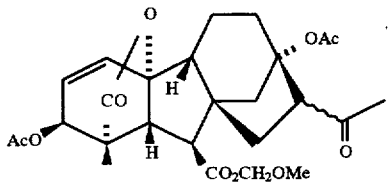

A solution of methyl lithium (6.95 ml, 1.25M in hexane) was added to a stirred solution of aldehyde (26) (4.26 g) in THF at -110° C. After 30 minutes the solution was allowed to warm to -60° C., acetic acid (1.5 ml) added, then the solution allowed to warm to room temperature. Ethyl acetate was added and after washing with brine, the solution dried over sodium sulfate, reduced to dryness and the residue chromatographed on silica gel. ent-3α,13-Diacetoxy-10β,17-dihydroxy-17-methyl-20-norgibberell-1-ene-7,19-dioic Acid 7 -Methoxymethyl Ester 19,10-Lactone (2.2 g, 50% yield) was eluted with 35% ethyl acetate in pentane. This material was oxidised directly to methyl ketone (39) by treating a solution in dichloromethane (305 ml) with pyridinium dichromate (5.2 g) and stirring in the dark at room temperature under an atmosphere of nitrogen for 22 h. The solvent was removed under reduced pressure and the residue extracted repeatedly with ethyl acetate, concentrated and chromatographed directly on silica gel. Ketone (39) (1.76 g, 66% yield) was eluted with 25% ethyl acetate in pentane. ent-10β,13-Dihydroxy-17,17-dimethyl-20-norgibberell-2-ene-7,19-dioic Acid 19,10-Lactone (40).

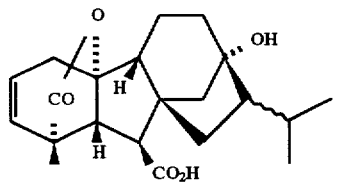

Acid (40) was prepared from ketone (39) by Wittig methylenation, hydrogenation, dehydration and deprotection by the procedures described for the conversion of aldehyde (26) via (27), (30), and (33) to gibberellin (36). After purification by preparative HPLC on a $C_{18}$ reverse phase column (Waters Nova-Pak HR C18 6 micron), eluting with water-methanol (70:30, containing 0.05% acetic acid) it displayed $^1H$ NMR ($CDCl_3/d_4$-MeOH, 4:1) δ0.85, 0.99 [2×3H, d, J=5.9 Hz, $CH(CH_3)_2$], 1.20 (3H, s, H-18), 2.31 (1H, dt, J=18.77, 2.6 Hz, H-1), 2.57 (1H, ddd, J=18.7, 3.4, 1.6 Hz, H'-1), 2.58, 2.74 (1H, Abd, J=9.8 Hz, H-5,6), 5.64 (1H, br d, J=6.4 Hz, H-3), 5.79 (1H, dt, J=6.4, 3.5 Hz, H-2).

EXAMPLE 38

General methods which may be applied to the preparation of the ring D-modified gibberellin compounds of the present invention include the following:

(i) gibberellin molecules containing a 1,2-double bond and a 3-β-hydroxyl group may be converted directly into 1α, 1β, 3α and 3β halogen derivatives by treatment with triphenylphosphine-carbon tetrachloride or triphenylphosphine-carbon tetrabromide or triphenylphosphine-hexachloroacetone mixtures (Dur et al., 1981a, 1981b; Banks and Cross, 1977; Cross and Simpson, 1981; Bearder et al., 1981);

(ii) various 1- and 3-halides may also be prepared by substitution of 3α and 3β methylsulfonyloxy gibberellins also containing a 1,2-double bond (Duri and Hanson, 1984; Corey et al., 1971);

(iii) 1β fluoro and 3β fluoro gibberellins may be prepared by treatment of gibberellic acid ($GA_3$) derivatives with 2-chloro-N,N-diethyl-1,1,2-trifluoroethylamine (Bakeson and Cross, 1974).

EXAMPLE 39

Activity in Stem Elongation and Floral Development in *Lolium temulentum*
(see Mander et al., 1995).

Materials and Methods

Plants

All plants of the Ceres strain of *Lolium temulentum* were grown in pots of perlite/vermiculite irrigated with nutrient solution each morning and water each afternoon. For the first 5 weeks from sowing they were held in short days (SD) of 8 h sunlight in shuttered glasshouse cabinets controlled at 25° C. by day and 20° C. by night. All tillers and lower main stem leaves were then cut off and the plants transferred to artificially lit cabinets also at 25° C./20° C. but with 8 h of light from fluorescent and incandescent lamps at an irradiance of 250 μmol of photosynthetically-active radiation (PAR) $m^{-2}s^{-1}$.

At 45–50 days of age the plants were usually given one long day (LD) by extending the exposure to incandescent lamps (≈12 μmol $m^{-2}s^{-1}$ PAR at plant height) for a further 16 h, which is sufficient to induce inflorescence initiation in all plants. They were then returned to SD for a further 3 weeks before dissection and scoring. There were 14 replicates per treatment, in 10 different experiments.

Test compound applications

The gibberellin derivatives (GAs) were applied in 95% ethanol/water, in a 10 μl drop to the uppermost fully-grown leaf blade on the afternoon of the LD. Doses were 1, 5 and 25 μg per plant but extending in some cases from 0.2 to 250 μg per plant. Control plants were treated with only 95% ethanol/water.

Scoring

Three weeks after the combined LD/GA treatments, the plants were dissected and shoot apex length and stage of inflorescence development were determined under a binocular microscope, and stem length measured. Floral scores in all instances bore a close relation to shoot apex length, as in previous studies, and the latter are presented as the more objective index of the stage of inflorescence development.

Results

A. Non-halogenated derivatives of 16,17 dihydro $GA_5$ 16-methyl-16,17-dihydro $GA_5$ This compound gave a highly significant inhibition of stem elongation even with 1 μg doses combined with only modest promotion of flowering at the higher doses.

17-methyl-16,17-dihydro $GA_5$ 16-ethyl dihydro $GA_5$ was a most powerful inhibitor of stem elongation, although not significantly more so than dihydro $GA_5$ or its 13-acetate. On flowering it had only a small promotive effect.

17-n-propyl-16,17-dihydro $GA_5$

Based on the results of only one experiment, this compound had no effect on stem elongation and only a slight promotive effect on flowering.

16,17-methano-16,17-dihydro $GA_5$

In two of the three experiments with this compound, it has been almost as inhibitory to stem elongation as dihydro $GA_5$, but rather less promotive of flowering, while in the third, it was as promotive of flowering as $GA_5$ and dihydro $GA_5$ but rather less inhibitory to stem elongation than the latter.

B. Halogenated derivatives of methano C 16,17-dihydro $GA_5$ monochloromethano C-16,17-dihydro $GA_5$ Based on the results of only one experiment, this compound strongly inhibited stem elongation after treatment (by 58%) for the 25 µg dose (compared with 36% for 25 µg of dihydro $GA_5$). Only at the 25 µg dose did it have a small promotive effect on shoot apex length.

dichloromethano C-16,17-dihydro $GA_5$

This compound has been applied in 4 experiments. It is a unique gibberellin derivative in that it strongly inhibited both stem elongation and flowering. For the 25 µg dose, stem elongation after treatment was reduced by 70% compared with the control, while dihydro $GA_5$ reduced it only by 46% in one experiment.

dichloromethano C-16,17-dihydro $GA_5$ acetate

This compound, prepared in the synthesis of the preceding compound, has been used in only one experiment, in which it was as inhibitory to elongation, and with a comparable effect on flowering, as dichloromethano dihydro $GA_5$.

dibromomethano C-16,17-dihydro $GA_5$

This has also been used only in one experiment, in which it was as inhibitory to stem elongation as the dichloro derivative, and comparable in its effect on flowering.

C. Derivatives of C-16,17-dihydro $GA_3$ 16,17-methano C-16,17-dihydro $GA_3$

Whereas methano dihydro $GA_5$ inhibited stem elongation significantly, methano dihydro $GA_3$ promoted it, although to a lesser extent than dihydro $GA_3$. The results in Table 1 are for plants held in SD, but comparable results were obtained with plants exposed to one LD. What they also show is that methano dihydro $GA_3$ was as effective in inducing flowering in SD as were dihydro $GA_3$, $GA_5$, $GA_3$ and one LD.

TABLE 1

Effect of several GAs and derivatives at 25 µg doses on stem and shoot apex length and score in plants of *L. temulentum* held throughout in short days. ± s.e.

| Treatment | Stem length (mm) | Apex length (mm) | Floral score |
|---|---|---|---|
| SD control | 193 ± 10 | 1.09 ± 0.03 | 0.36 ± 0.20 |
| SD ± $GA_3$ | 293 ± 12 | 2.02 ± 0.09 | 4.92 ± 0.26 |
| SD ± $GA_5$ | 250 ± 14 | 2.18 ± 0.13 | 5.29 ± 0.44 |
| SD ± dihydro $GA_3$ | 230 ± 7 | 2.42 ± 0.12 | 6.0 ± 0.35 |
| SD ± methano dihydro $GA_3$ | 214 ± 6 | 2.40 ± 0.11 | 5.85 ± 0.10 |
| SD ± bromomethano dihydro $GA_3$ | 170 ± 7 | 1.15 ± 0.05 | 0.62 ± 0.27 |
| SD ± dibromomethano dihydro $GA_3$ | 187 ± 13 | 1.19 ± 0.11 | 1.00 ± 0.63 |
| ILD control | 191 ± 7 | 2.22 ± 0.11 | 6.0 ± 0.18 | monochloromethano C-16,17-dihydro $GA_3$

In two experiments this compound was inactive for stem elongation, neither promoting nor inhibiting it at any dosage, but was highly florigenic.

dichloromethano C-16,17-dihydro $GA_3$

In contrast with the monochloro derivative, the dichloro form had no effect on flowering as well as none on stem elongation.

monobromomethano C-16,17-dihydro $GA_3$

Like its chlorinated counterpart, this compound had no significant effect on stem elongation, but differed in having no promotive effect on flowering (Table 1).

dibromomethano C-16,17-dihydro $GA_3$

This compound, like its chlorinated counterpart, had no effect on either stem or shoot apex length (Table 1).

D. dichloromethano C-16,17-dihydro $GA_{20}$

In one experiment this compound had only a slight promotive effect on flowering, but inhibited stem elongation to almost the same extent as dichloromethano dihydro $GA_5$ and more than dihydro $GA_5$.

E. Rice

Inhibitory effects on $GA_{20}$-induced shoot elongation by three of the above compounds, 16,17-dichloromethano C-16,17-dihydro $GA_5$, 16,17-methano C-16,17-dihydro $GA_5$ and 16-methyl-16,17-dihydro $GA_5$ yielded results in parallel those in Lolium (see above).

F. Wild Oat

Inhibitory effects on shoot elongation and delayed flowering by dichloromethano C-16,17-dihydro $GA_5$ and its C-13 acetate are in parallel to those in Lolium (see above).

DISCUSSION

The results presented here confirm the very different structural specificities for stem elongation vis-a-vis flowering found earlier among the GAs (Evans et al., 1990). Some of the GA derivatives examined here had no effect on either stem elongation or flowering, such as dichloro- and dibromo methano dihydro $GA_3$ (Table 1).

Several compounds promoted flowering strongly but had no effect on stem elongation, such as monochloromethano dihydro $GA_3$. This is an important category in relation to the role of endogenous gibberellins in the flowering of *L. temulentum* because, at least until 3 weeks after treatment, plants exposed to an inductive LD display a marked increase in shoot apex length and floral score without significant increase in stem length (e.g. Table 1).

A novel, and potentially useful, combination of effects of GA derivatives in this study is the strong inhibitory effect on both stem elongation and inflorescence development in this grass by dichloromethano dihydro $GA_5$.

Considering only the effect of the dihydro $GA_5$ derivatives on Lolium, 17-methyl-dihydro $GA_5$ and 16-methyl-dihydro $GA_5$ were more inhibitory to stem elongation than 16,17-methano dihydro $GA_5$, being comparable in this respect with dihydro $GA_5$ itself. For dwarf rice leaf sheath elongation induced by several gibberellins without a C-13β hydroxyl, a comparable ordering of growth reduction occurred, except that all novel ring D-modified gibberellins were more effective than C-16,17-dihydro fibberellins. However, the addition of one chlorine to methano dihydro $GA_5$ increased the reduction in stem growth after treatment to 58% (cf. 36% for dihydro $GA_5$), while dichloromethano dihydro $GA_5$ inhibited elongation by 70% or more. Comparable growth reductions were also obtained for dichloromethano dihydro $GA_5$ on dwarf rice sheath growth (see below) and wild oat height and shoot biomass (data not shown).

Florigenicity responded differently to variation among the dihydro $GA_5$ derivatives. It was reduced by the presence of a 13-acetate group (which did not affect stem elongation), as could be expected given the promotive effect of C-13 hydroxyl (Evans et al., 1990). The florigenicity of dihydro $GA_5$ was not significantly reduced with the methano derivatives whereas it was with the 16-methyl, 17-methyl and 17-n-propyl derivatives of dihydro $GA_5$. The addition of one chlorine to methano dihydro $GA_5$ reduced the flowering response only slightly, but the addition of two chlorines converted a promotive effect into a strongly inhibitory one, yielding a compound of potential value as both a growth and flowering retardant, at least for cool season grass swards and grassy weeds.

EXAMPLE 40

Activity on Turfgrass (see Mander et al., 1995)

The effects of the GA compounds, 16,17-dihydro-$GA_5$, 17-methyl-16,17-dihydro-$GA_5$ and 16α, 17-dichloromethano-dihydro-$GA_5$ (referred to as DCM-$GA_5$) on turf-related aspects of the growth of *Poa pratensis* and *Lolium perenne*, and on turf predominantly composed of these two species, has been investigated.

A. Materials and Methods (a) Trials in the field.

Two trials were carried out in 1994 on commercial turf made available by Canturf at their irrigated turf farm near Bungendore, the first in autumn (March-April) and the second in spring-early summer (September-December). In both cases the experiments were laid out on a uniform and level mature turf which had been sown with a 20:80 mix of *Poa pratensis* cv. Bronco and *Lolium perenne* cv. SR4100 and regularly fertilised and irrigated. Turf growth rates in the autumn experiment controls were only 2–5 g $m^{-2}d^{-1}$, but reached 10.2 g m-2 $d^{-1}$ during the experiment in spring.

In both experiments there were 10 treatments replicated 5 times in a 10 by 5 array so that each column constituted a replicate and pairs of rows constituted replicates. Alleys 0.5 m wide between the plots were cut lower than the plots which were then mown, at approximately weekly intervals, to a standard height of 55 mm. The harvested area of each plot was 0.845 $m^2$. Turf growth was determined from the oven-dry weight of the clippings, presented here as a percentage of that of the control plots, ± the standard errors.

All plots were sprayed only once, with 300 ml $m^{-2}$ of 5% ethanol in water plus 0.1% Agral on the controls, or with the added gibberellin derivative on the treatments, with solutions brought to pH 6.8. In the first experiment, the treatment solutions contained 2, 7, 20, 70 or 200 ppm of DCM-$GA_5$, 125 ppm of 16,17-dihydro $GA_5$ (exo) or 30, 200 or 700 ppm of Primo™. In the second experiment, treatments were with 10, 33, 100 or 330 ppm DCM-$GA_5$, 100 ppm of 17-methyl-16,17-dihydro-$GA_5$ or 33, 330 or 700 ppm of Primo™ (Trinexapac-ethyl; Ciba-Geigy, Australia) (100 ppm is equivalent to application of 300 g $ha^{-1}$). In the first experiment all plots were sprayed, inside guard sheets, on 15 Mar. 1994 in fine weather. In the second experiment, all plots had been mown and harvested three times before spraying on 19 Oct. 1994. Several hours later there was 4 mm of rain.

(b) Phytotron experiments with *Poa pratensis*.

Five experiments in CERES, the Canberra phytotron, have been with plants grown singly in 8 cm plastic pots in a 1:1 mixture of perlite and vermiculite under controlled temperature and daylength conditions. The plants were watered with nutrient solution each morning and water each afternoon. All plants were exposed to natural daylight for 8 h each day until the sixth leaf appeared, after which various daylengths were imposed by extending the 8 h period in daylight with low irradiance light (~16 µmol PAR $m^{-20}$ $s^{-1}$) from incandescent lamps. There were 3 photoperiods in 3 experiments, 2 in the other 2. Cabinet temperatures were 18° C. throughout the daylight period and 13° C. during the photoperiod extensions and darkness.

Seed of *Poa pratensis* cv. Holt, origin 69° N, from the Norwegian Basic Seed Centre was used in all experiments, and the behaviour of this line was compared with that of cv. Bronco in the last experiment. At each harvest 12–14 replicate plants were removed from each treatment, at intervals of one week or more, for the measurement of plant height, blade length of selected main-stem leaves, the number of main-stem leaves, tiller number, shoot apex length and stage, shoot dry weight and (in one experiment) root dry weight.

All treatments with the GA derivatives were applied, only once, at the time of transition to the various photoperiod treatments. Applications of 1, 5 or 25 µg of the GA in a single 10 µl drop of 95% ethanol/water were made to the middle of the uppermost leaf blade of each plant. Controls were treated with 10 µl of ethanol/water.

(c) Phytotron experiment on water use by *Lolium perenne* swards.

Seeds of perennial ryegrass cv. SR4100 were sown in large (12.5 cm diameter) pots of 1:1 perlite/vermiculite at a density sufficient to ensure a closed sward by the time each plant had 3 tillers, and grown in a greenhouse at 24°/19° C. (day/night) under a daylength of 16 h. Nutrient solution and water were provided daily. At the time of treatment the swards were cut to a height of 35 mm above the growing medium, which was then brought to field capacity. Each pot was then sprayed with 5 ml of ether 5% ethanol/95% water plus 0.1% Agral wetting agent, or with the same solution containing 350 mg $L^{-1}$ of DCM-$GA_5$, and returned to the glasshouse. There were 8 replicate swards per treatment. Water use was followed gravimetrically, the pots being rewatered every 24 h to their initial weight.

B. Results (a) Turf trials in the field.

The two field trials on commercial turf at Bungendore, the first in autumn and the second in spring, gave broadly similar results. More directly comparable dose rates for DCM-$GA_5$ and Primo™ were used in the second experiment. Prior to the spray treatments weekly growth on all plots was comparable, but within one week of spraying there was a highly significant inhibition of growth which remained strong for 4–6 weeks and was then followed by a period of accelerated growth. In all cases the inhibition by DCM-$GA_5$ and Primo™ was much greater than the rebound but there was, nevertheless, quite a close positive relationship between the maximum % inhibition of growth and the maximum % promotion across doses and retardants, especially for DCM-$GA_5$.

For both retardants, the greater the dose the greater the maximum extent of inhibition of regrowth and the longer the inhibition lasted. Recovery back to the level of the controls occurred after 34 and 44 days with 33 ppm sprays of DCM-$GA_5$ and Primo™ respectively, and after 45 and 50 days respectively with 330 ppm sprays. One week after spraying, the two retardants were inhibitory to a comparable degree, but the inhibition by DCM-$GA_5$ did not increase as much over the next 2–4 weeks as it did with Primo™.

The effects of concentration of the two compounds on regrowth in the second week after cutting in the two turf experiments were also compared. For both retardants, the inhibition of growth was more or less log-linear with dose. In the second (spring) experiment the two retardants were highly comparable in their effectiveness, whereas in the earlier (autumn) experiment about 7 times more Primo™ was needed to get inhibition comparable with that of DCM-GA$_5$. This inconsistency between the two experiments may be a seasonal effect: turf growth rates were much higher in the spring experiment. However, it could also be associated with the fact that in the first experiment fine weather prevailed during and for several days after spraying whereas in the second one spraying took place under overcast conditions and was followed several hours later by 4 mm of rain.

Inflorescence production under the weekly mowing regime was too sparse in both experiments to observe any differences in its inhibition by Primo™ and DCM-GA$_5$ although, on the evidence of experiments with Lolium (see Example 37), DCM-GA$_5$ should be more effective. One difference that was apparent between the two compounds, in both experiments, was the tendency for Primo™ to cause browning (discolouration) of the turf at the higher doses.

In the first turf experiment, 16,17-dihydro-GA$_5$ was much less inhibitory at the one dose used than its chlorinated derivative DCM-GA$_5$, while in the second experiment 17-methyl-16,17-dihydro-GA$_5$ was of comparable effectiveness to Primo™ and DCM-GA$_5$.

(b) Phytotron experiments with *Poa pratensis*.

Daylength had a large effect on leaf blade length in cv. Holt in all 5 experiments, the longest blade in SD being on average only 45% as long as that in the longest photoperiod. In cv. Bronco the longest main-stem leaf in 10 h photoperiods was 47% of that in 15 h ones compared with 44% in cv. Holt. The corresponding figures for final plant height were 44% and 47%. Thus the *Poa pratensis* component of the turf experiments, being highly sensitive to daylength for leaf elongation, should also be sensitive to GA status.

The two cultivars differed, however, in their growth and in their responses to retardants which inhibit GA$_1$ biosynthesis. Neither compound significantly reduced final leaf number and the rate of leaf appearance on the main stem, although they were greater in SD than in LD. The length of the tenth main-stem leaf blade was reduced by SD and by retardant applications in LD to a comparable extent, with Primo™ being rather more effective than DCM-GA$_5$ at a dose of 25 µg per plant, and also at a dose of 5 µg per plant. Plant height was also reduced by SD, and to a lesser extent by the retardants, with Primo™ being more effective than DCM-GA$_5$. The rate of increase in plant height in the second week after treatment was greatly reduced by SD and by both compounds in LD, but only by Primo™ in SD with cv. Bronco. Tillering was greater in SD than in LD and was significantly increased in LD by both compounds. Dry weight of the shoots was measured only at final harvest 39 days after treatment: with cv. Holt, DCM-GA$_5$ had no significant effect on shoot dry weight in either cultivar or either daylength, whereas Primo™ significantly reduced it in all cases except cv. Bronco in LD.

Across all experiments, the order of effectiveness as growth retardants, at a dose of 25 µg was Primo™>DCM-GA$_5$>dihydro GA$_5$, partly because Primo™ appeared to maintain its inhibitory effect on leaf elongation rate for a longer time than DCM-GA$_5$ (e.g. two weeks cf. one in 15 h photoperiod), as in the turf experiments. At the lower doses, however, DCM-GA$_5$ was as effective as Primo™ in several instances.

(c) Phytotron experiment on water use by mini-swards of *Lolium perenne*.

The effect of spraying small swards of perennial ryegrass SR4100 once with either DCM-GA$_5$ or Primo™ on their daily water use in a controlled-temperature (24°/19° C.) glasshouse was examined in only one experiment. Both retardants resulted in a highly significant reduction in water use by the fourth day after swards were sprayed, but this lasted only a few days.

C. Discussion

In the experiments reported here with both single plants grown in controlled environments and turf growing in the field in both spring and autumn, the inhibition of turf height growth by some derivatives of 16,17-dihydro-GA$_5$ is comparable with that achieved by the commercial retardant Primo™ (Trinexapacethyl). In the Bungendore turf experiments, the initial inhibition of shoot elongation was as great or greater with DCM-GA$_5$ as with Primo™ at the same dose. The effect of the single spray treatment was somewhat longer lasting with Primo™, but it reduced plant dry weight and caused some browning of the sward which DCM-GA$_5$ did not. Both compounds caused a temporary reduction in water use by mini-swards in the phytotron. Both compounds also caused a substantial "rebound" in growth about 8 weeks after spraying, which was reversed in the case of DCM-GA$_5$ with a second spraying.

The finding that both Primo™ and DCM-GA$_5$ reduced leaf blade length in LD to near that of untreated leaves in SD suggests that most of the additional leaf elongation in LD was associated with 3β-hydroxylation of GA$_{20}$ to GA$_1$. However, despite the similarities in their probable mode of action by inhibiting the 3β-hydroxylation of gibberellins, and in their overall effects and dose response, as well as in neither of them reducing the rate of leaf appearance, there were some differences between Primo™ and DCM-GA$_5$ in their effects. There were also differences in the responses of the two cultivars of *Poa pratensis*, which may influence their overall usefulness as retardants. For example, although daylength had a similar effect on leaf blade elongation in the two *Poa pratensis* cultivars, the length of the youngest fully-emerged blades in SD was unaffected by either retardant in cv. Holt but inhibited by both of them in cv. Bronco, as was shoot dry weight by Primo™.

The experimental results with single plants also differed in some ways from those with turf in the field, particularly in the greater relative inhibition by Primo™ compared with DCM-GA$_5$ in single plants, although this was less marked at the lower dose rates. Nevertheless, it is quite clear that the novel 16,17-dihydro-GA$_5$ derivatives may have a useful role as turf grass retardants which can reduce not only leaf elongation but also inflorescence production in swards without discolouration or loss of dry weight and density.

EXAMPLE 41

Retardation of Growth of the Second Leaf Sheath in Rice (cv. Tan-ginbozu).

Dwarf rice cv. Tan-ginbozu, partially blocked for endogenous gibberellin synthesis very early in the biosynthetic pathway, is further reduced in endogenous bioactive gibberellin by soaking the seed first in a potent chemical plant growth retardant (Uniconazole) which also acts very early in the gibberellin biosynthetic pathway.

Then, these extremely gibberellin deficient rice plants have applied to them various gibberellins in microdrops of ½ microliter, at 1, 10 or 100 nanograms per plant to induce leaf sheath growth. Growth-promotive gibberellins utilised include:

gibberellin A$_1$—an actual "effectoer" of rice sheath elongation gibberellin A$_{20}$—a precursor to gibberellin A1. (Gibberellin A$_{20}$, which is C-2,3-dihydro, requires hydroxylation at C-3β to form gibberellin A1).

gibberellin $A_9$—a precursor to gibberellin $A_4$. (Gibberellin $A_4$ may be biologically active in promoting sheath growth of rice per se, or may be converted to gibberellin A1).

2,3-didehydro gibberellin $A_9$—a likely precursor to gibberellin $A_7$. (Gibberellin $A_7$ may be biologically active in promoting sheath growth of rice per se, as no known metabolites of it have been found in the higher plants, as yet.)

The above growth-promotive gibberellins are then challenged with a ring D-modified gibberellin test compound, resulting in the inhibition of the "gibberellin-induced growth" (relative to control plants receiving the gibberellin alone). The mechanism of action of these test compounds appears to be the competitive inhibition of C-3β hydroxylation, thereby preventing formation of the final gibberellin which is a "growth effector" per se.

A comparison of the ring D-modified gibberellin test compounds with the previously known endo- C-16,17-dihydro gibberellin $A_5$ (see Evans et al. 1994a and International Patent Application No. PCT/AU92/00426) demonstrates the striking increase in efficacy for a number of the test compounds, relative to the C-16,17-dihydro gibberellins.

Figure 1B:
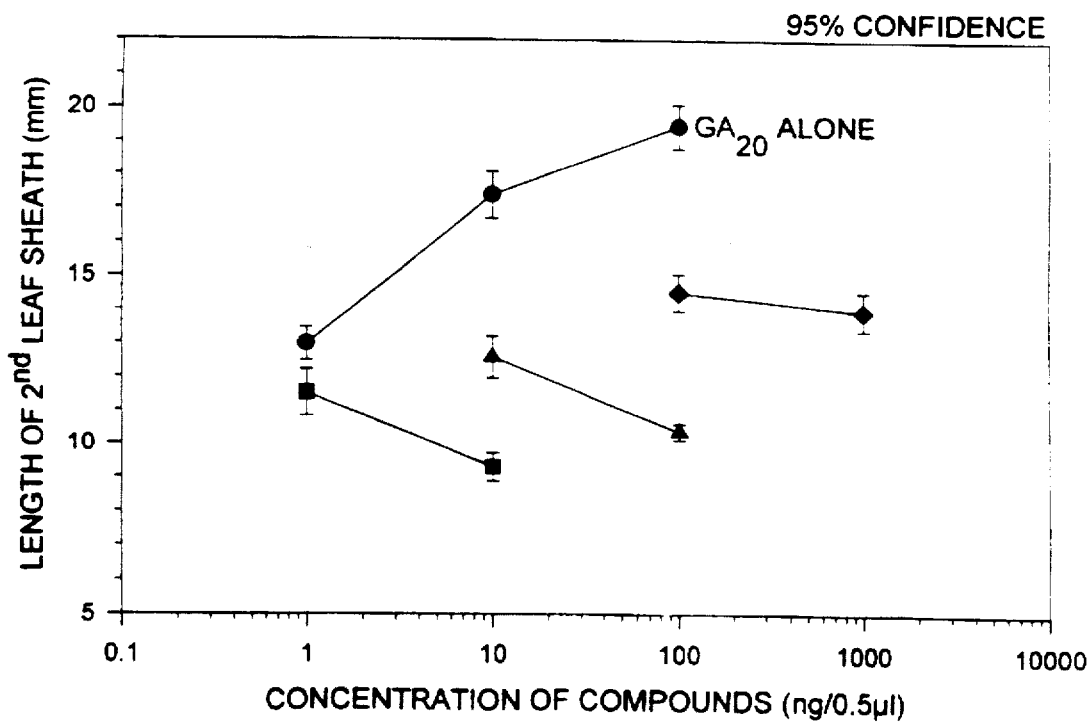

FIGS. 1a and 1b show the use of two test compounds, dichloromethano-16,17-dihydro gibberellin $A_5$ (DCM-GA$_5$) and endo-C-16,17-dihydro $GA_5$ to challenge gibberellin $A_{20}$-induced growth.

Growth induced by gibberellin $A_{20}$ alone is shown in solid circles. The error bars constitute 95% Confidence Limits of Probability. the test compound is applied to gibberellin $A_{20}$-treated rice plants at 1X or 10X the level of applied $GA_{20}$. Thus, solid squares (FIG. 1a) represent 1 ng or 10 ng of DCM-GA$_5$ used to challenge 1 ng of gibberellin $A_{20}$, etc. A similar protocol was used for the endo-C-16,17-dihydro gibberellin $A_5$ comparison. In all three tests, DCM-GA$_5$ is very growth retardive against $GA_{20}$ induced growth, and is more growth retardive at most doses than is endo-C-16,17-dihydro gibberellin $A_5$.

Thus, dichloromethano-16,17-dihydro gibberellin $A_5$ showed remarkable and unexpectedly high growth retardive abilities against gibberellin $A_{20}$-induced growth relative to $GA_{20}$-treated controls and relative to endo-C-16,17-dihydro gibberellin $A_5$.

Responses for various test compounds against controls treated with $GA_{20}$, $GA_9$, 2,3-didehydro $GA_9$ and $GA_1$ are summarised in the Table. The method of treatment, doses used and measurements were identical to those above for $GA_{20}$. The response is only given for a 10 ng dose of the growth promotory gibberellin challenged with 100 ng of the test compound. The pattern of responses at all other doses conformed with the response at this dose.

Other ring D-modified gibberellin test compounds were also more growth retardive than endo-C-16,17-dihydro $GA_5$ at most doses and when tested against $GA_{20}$, $GA_9$ or 2,3-didehydro $GA_9$ (see Table 2). Loss of inhibitory activity was evident with 16,17-methano-16,17-dihydro $GA_5$ and dichloromethano-16,17-dihydro $GA_{20}$ (the C-2,3-dihydro form of DCM $GA_5$).

The variation in % of control growth between experiments precludes generalisations as to the efficacy when comparing DCM GA$_5$ with the ethyl, propyl or butyl forms and with C-16 gem dimethyl GA$_5$. They all inhibit growth to similar extents. The acetate form of endo C-16,17-dihydro GA$_5$ was slightly more active than endo 16,17-dihydro GA$_5$.

When 17-methyl-16,17-dihydro GA$_5$ was used to challenge gibberellin $A_1$ induced growth it was inactive, although it was active against gibberellin $A_{20}$ (see Table 2). $GA_1$ is an "effector" of growth per se, and already possesses the important C-3β-hydroxy group. This is strong evidence that the mechanism of action of ring D-modified gibberellins in retarding shoot growth lies in the inhibition of C-3β hydroxylation, and not in competing against the action of an "effector" gibberellin as also noted by Evans et al. (1994).

The differences in growth retarding activity with variants in the ring A indicate the benefit of the C-2,3 didehydro vs. C-2,3 dihydro. However, with C-16,17 dihydro gibberellins, both C-16,17-dihydro GA$_5$ and its ring A variant C-16, 17-dihydro $GA_{20}$ were active in Lolium (Evans et al., 1994b).

The effectiveness on addition of the two chlorine atoms to the C-16,17 methano group is remarkable and unexpected, as growth retarding capability is enhanced several fold (see Table 2 and findings above for Lolium).

TABLE 2

| Test Compound | % of GA Control Growth at 10 ng dose (values for one or more experiments) |
|---|---|
| | vs. $GA_{20}$ |
| dichloromethano-16, 17-dihydro GA$_5$ (9) | 54,65,60,60 |
| dichloromethano-16, 17-dihydro GA$_{20}$ (9a) | 81 |
| 17 methyl-dihydro GA$_5$ (36) (exo/endo mixture) | 57 |
| exo 17-methyl-dihydro GA$_5$ (36a) | 57 |
| endo 17-ethyl-dihydro GA$_5$ (37b) | 57 |
| exo 17-n-propyl-dihydro GA$_5$ (38a) | 60 |
| C-16-methyl 16, 17-dihydro-GA$_5$ (21) | 55 |
| endo C-16, 17-dihydro GA$_5$ | 73,62,69 |
| endo C-16, 17-dihydro GA$_5$ 13 acetate | 58 |
| | vs. $GA_9$ |
| dichloro methano-16, 17-dihydro GA$_5$ (9) | 63,57,49,59 |
| dichloromethano-16, 17-dihydro GA$_{20}$ (9a) | 79 |
| 17 methyl-dihydro GA$_5$ (36) (exo/endo mixture) | 63,62 |
| exo 17-methyl-dihydro GA$_5$ (36a) | 63 |
| endo 17-ethyl-dihydro GA$_5$ (37b) | 56 |
| exo 17-n-propyl-dihydro GA$_5$ (38a) | 56 |
| C-16-methyl-16, 17-dihydro-GA$_5$ (21) | 51,55 |
| C-16, 17-methano-16, 17-dihydro GA$_5$ (17) | 70 |
| endo C-16, 17-dihydro GA$_5$ | 67,70,72 |
| endo C-16, 17-dihydro GA$_5$ C-13 acetate | 62,71 |
| | vs. 2,3 didehydro $GA_9$ |
| dichloromethano-16, 17-dihydro GA$_5$ (9) | 65,63 |
| 17 methyl-dihydro GA$_5$ (36) (exo/endo mixture) | 65 |
| C-16-methyl-16, 17-dihydro-GA$_5$ (21) | 75 |
| C-16, 17-methano-16, 17-dihydro GA$_5$ (17) | 112 |
| endo, C-16, 17-dihydro GA$_5$ | 73 |
| | vs. $GA_1$ |
| 17-methyl-dihydro GA$_5$ (36) (exo/endo mixture) | 101 |

EXAMPLE 43

Growth Inhibition of Turfgrasses

The effect of DCM-GA$_5$ as a plant growth regulator on yields of Kentucky bluegrass was assessed in field tests in Ohio, USA.

Methods:

The experimental plant growth regulator DCM-GA$_5$, was dissolved in ethanol, then the solution was mixed with water at the rate of one part solution in 20 parts water. The rates of the experimental plant growth regulator applied were 0.15, 0.3 and 0.75 lb active ingredient per acre (ai/A). The plot size was 5 ft×10 ft with 3 replications and a volume of 45 gallons/A.

Results Summary:

Growth inhibition of Kentucky bluegrass was significant compared to untreated control (UTC) plots with all rates of DCM-GA$_5$ as seen in the Table 3 below. Inhibition was increased as rate increased compared to UTC and residual activity was significant through 38 days after treatment (DAT).

TABLE 3

| Treatment | Rate | Yield DAT* | | | | | | |
|---|---|---|---|---|---|---|---|---|
| | | 6 | 12 | 18 | 26 | 31 | 38 | 44 |
| UTC | — | 114 | 82 | 80 | 56 | 80 | 107 | 145 |
| DCM-GA$_5$ | 0.15 | 49 | 15 | 20 | 37 | 84 | 128 | 161 |
| DCM-GA$_5$ | 0.30 | 43 | 10 | 6 | 13 | 49 | 107 | 178 |
| DCM-GA$_5$ | 0.75 | 51 | 8 | 4 | 7 | 30 | 63 | 122 |

* Yields measured in grams per 17.5 (ft)$^2$ at 6, 12, 18, 26, 31, 38 and 44 days after treatment (DAT).

REFERENCES:

Adams, R., Kerber, E., Pfister, K., Weiler, E. W. (1992). Studies on the action of the new growth retardant CGA 163935 (Cimetacarb). pp. 818–827. In: C. M. Karssen, L. C. VanLoon, D. Vreugdenhil (eds). Progress in Plant Growth Regulation. Kluwer, Dordrecht.

Banks, R. E. and Cross, B. E. (1977). *J. Chem. Soc. Perkin Trans.* 1:512.

Bateson, J. H. and Cross, B. E. (1974). *J. Chem. Soc. Perkin Trans.* 1:2409.

Bearder, J. R., Kirkwood, P. S. and MacMillan, J. (1981). *J. Chem. Soc. Perkin Trans.* 1:672.

Corey, E. J., Brennan, T. M. and Carney, R. L. (1971). *J. Am. Chem. Soc.* 93:7316.

Cross, B. E. and Simpson, I. C. (1981). *J. Chem. Soc. Perkin Trans.* 1:98.

Duri, Z. J., Fraga, B. M. and Hanson, J. R. (1981a). *J. Chem. Soc. Perkin Trans.* 1:161.

Duri, J. Z., Fraga, Braulio M. and Hanson, J. R. (1981b). *J. Chem. Soc. Perkin Trans.* 1:3016.

Duri, J. Z. and Hanson, J. R. (1984). *J. Chem. Soc. Perkin Trans.* 1:603.

Evans, L. T. (1964). Inflorescence initiation in *Lolium temulentum* L.V. The role of auxins and gibberellins. *Aust. J. Biol. Sci.* 17:10–23.

Evans, L. T. (1969). Inflorescence initiation in *Lolium temulentum* L. XIII. The role of gibberellins. *Aust. J. Biol. Sci.* 22:773–786.

Evans, L. T., King, R. W., Chu, A., Mander, L. N., Pharis, R. P. (1990). Gibberellin structure and florigenic activity in *Lolium temulentum*, a long-day plant. *Planta.* 182:96–106.

Evans, L. T., King, R. W., Mander, L. N. and Pharis, R. P. (1994a). The relative significance for stem elongation and flowering in *Lolium temulentum* of 3β-hydroxylation of gibberellins. *Planta.* 192:130–136.

Evans, L. T., King, R. W., Mander, L. N. and Pharis, R. P. (1994b). The differential effects of C-16,17-dihydro gibberellins and related compounds on stem elongation and flowering in *Lolium temulentum* L. *Planta.* 193:107–114.

Johnson, B. J. (1990). Influence of frequency and dates of plant growth regulator applications to centipedegrass on seedhead formation and turf quality. *J. Am. Hort. Sci.* 115:412–416.

Johnson, B. J. (1993). Frequency of plant growth regulator and mowing treatments : effects on injury and suppression of centipedegrass. *Agron. J.* 85:276–280.

Kaufman, J. E. (1990). Practical considerations in using growth regulators on turfgrass. pp. 585–594. In: Plant Growth Substances, 1988. R. P. Pharis and S. B. Rood (eds). Springer-Verlag, Berlin.

Lang, A. (1965). Physiology of flower initiation. In: Encyclopedia of plant physiology, Vol. XV. pt.1. pp.1380–1536. Ruhland, W., ed. Springer, Berlin, Heidelberg, New York.

Mander, L. N., Camp, D., Evans, L. T., King, R. W., Pharis, R. P., Sherborn, M. and Twitchin, B. (1995). Designer gibberellins : the quest for specific activity. *Acta Hortic.* (in press).

Pharis, R. P., King, R. W. (1985). Gibberellins and reproductive development in seed plants. *Annu. Rev. Plant Physiol.* 36:517–568.

Sander, K. W. and Hensley, J. R. (1993). Reversal of Prinexapac-ethyl (Primo™) suppression by Porgib®. pp.34–38. In: Proceedings 5th Annual Conference Western Plant Growth Regulator Society, USA.

Spak, D. R., DiPaola, J. M., Lewis, W. M. and Anderson, C. E. (1993). Tall fescue sward dynamics: II. Influence of four plant growth regulators. *Crop Sci.* 33:304–310.

Takagi, M., Pearce, D. W., Janzen, L. M. and Pharis, R. P. (1994). Effect of exo-16,17-dihydro-gibberellin A$_5$ on gibberellin A$_{20}$ metabolism in seedlings of dwarf rice (*Oryza sativa* L. cv. Tan-ginbozu). *Plant Growth Regulation* 15:207–213.

Zeevaart, J. A. D. (1983). Gibberellins and flowering. In: The Biochemistry and Physiology of Gibberellins. Vol. II, pp.333–374. Crozier, A., ed. Praeger, New York.

We claim:

1. A ring D-modified gibberellin compound of the general formula IA, IB or IC, as follows:

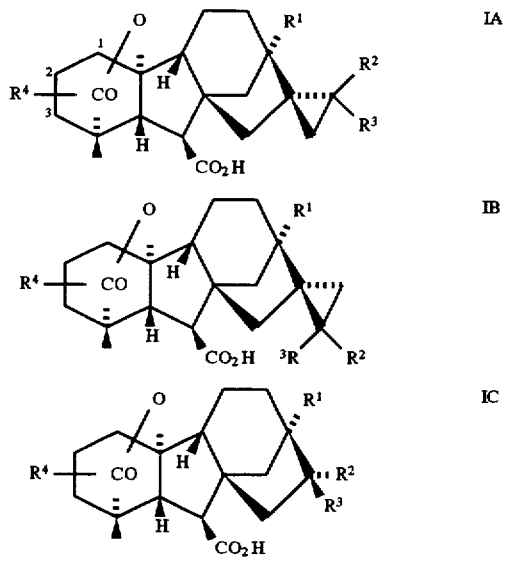

wherein, in compounds of the general formula 1A or 1B, R$^1$ represents H or OH; and R$^2$ and R$^3$, which may be the same or different, each represents H, F, Cl, Br, lower (C$_{1-6}$) alkyl, lower (C$_{2-6}$) alkenyl or lower (C$_{3-6}$) cycloalkyl;

and R$^4$ indicates that the A ring may be (i) unfunctionalised, or (ii) contain a 1,2-double bond or 2,3-double bond, or (iii) contain a 3α- or 3β-OH, F, Cl or Br group with or without a 1,2-double bond, or (iv) contain a 1α- or 1β-OH, F, Cl or Br group with or without a 2,3-double bond, and wherein in compounds of the general formula 1C, $R^1$ represents H or OH; and $R^2$ and $R^3$, which may be the same or different, each represents H, F, Cl, Br, lower ($C_{1-6}$) alkyl, lower ($C_{2-6}$) alkenyl, lower ($C_{3-6}$) cycloalkyl, or $CH_2X$ wherein X is F, Cl or Br;

and $R^4$ indicates that the A ring may be (i) unfunctionalised, or (ii) contain a 1,2-double bond or 2,3-double bond, or (iii) contain a 3α- or 3β-OH, F, Cl or Br group with or without a 1,2-double bond, or (iv) contain a 1α- or 1β-OH, F, Cl or Br group with or without a 2,3-double bond;

with the proviso that in compounds of the general formula 1C:

(i) $R^2$ and $R^3$ are not both H;

(ii) if $R^2$ is H then $R^3$ is not methyl, and if $R^3$ is H then $R^2$ is not methyl;

(iii) $R^2$ is not Cl or Br when $R^3$ is chloromethyl or bromomethyl and the A ring contains a 3β-OH, and $R^3$ is not Cl or Br when $R^2$ is chloromethyl or bromomethyl and the A ring contains a 3β-OH;

or an ester or ether of a compound of general formulae 1A to 1C having a 1-OH, 3-OH and/or 13-OH group, and/or an ester or salt of a compound of general formulae 1A to 1C having a 7-COOH group.

2. A compound according to claim 1, wherein said ester is a lower carboxylic acid ester, said ether is a lower alkyl or substituted lower alkyl ether, and/or said salt is an alkali or alkaline earth metal salt.

3. A compound according to claim 1 or claim 2, which is a compound of the $GA_1$, $GA_4$, $GA_7$ or $GA_9$ series of gibberellins.

4. A compound according to claim 1 or claim 2, which is a compound of the $GA_3$, $GA_5$ or $GA_{20}$ series of gibberellins.

5. A compound according to claim 1, which is selected from:

methano-16,17-dihydro gibberellin $A_3$ methano-16,17-dihydro gibberellin $A_5$ methano-16,17-dihydro gibberellin $A_{20}$ monochloro- or monobromo-methano-16,17-dihydro gibberellin $A_3$ monochloro- or monobromo-methano-16,17-dihydro gibberellin $A_5$ monochloro- or monobromo-methano-16,17-dihydro gibberellin $A_{20}$ dichloro- or dibromo-methano-16,17-dihydro gibberellin $A_3$ dichloro- or dibromo-methano-16,17-dihydro gibberellin $A_5$ dichloro- or dibromo-methano-16,17-dihydro gibberellin $A_{20}$ or an ester, ether or salt thereof.

6. Dichloromethano-16,17-dihydro gibberellin $A_5$ or an ester, ether or salt thereof.

7. A compound according to claim 1, which is selected from:

16-methyl-16,17-dihydro gibberellin $A_5$ 17-methyl-16,17-dihydro gibberellin $A_5$ 17-ethyl-16,17-dihydro gibberellin $A_5$ 17-n-propyl-16,17-dihydro gibberellin $A_5$.

8. A method for promoting or inducing a desired tissue morphology and/or physiological state in a plant, which comprises applying to the plant or plant tissue an effective amount of a compound according to any of claim 1.

9. A method according to claim 8, wherein the plant tissue to which the active compound is applied is a cutting, root, bulb, corm, tuber, rhizome or seed.

10. A composition for the treatment of a plant or plant tissue, which comprises an effective amount of a compound according to any of claim 1, together with an agriculturally- or horticulturally-acceptable carrier or diluent.

\* \* \* \* \*